United States Patent
Lanes et al.

(10) Patent No.: US 8,551,753 B2
(45) Date of Patent: Oct. 8, 2013

(54) METHOD OF REMOVING NUCLEIC ACID CONTAMINATION IN REVERSE TRANSCRIPTION AND AMPLIFICATION REACTIONS

(75) Inventors: Olav Lanes, Tromsø (NO); Morten Elde, Tromsø (NO); Dag Rune Gjellesvik, Tromsø (NO)

(73) Assignee: Biotec Pharmacon ASA, Tromso (NO)

( * ) Notice: Subject to any disclaimer, the term of this patent is extended or adjusted under 35 U.S.C. 154(b) by 67 days.

(21) Appl. No.: 12/840,552

(22) Filed: Jul. 21, 2010

(65) Prior Publication Data

US 2011/0020878 A1 Jan. 27, 2011

Related U.S. Application Data

(60) Provisional application No. 61/235,177, filed on Aug. 19, 2009.

(51) Int. Cl.
*C12N 9/22* (2006.01)
*C12P 19/34* (2006.01)

(52) U.S. Cl.
USPC ......... 435/199; 435/194; 435/91.1; 435/91.2; 435/91.53; 530/350

(58) Field of Classification Search
None
See application file for complete search history.

(56) References Cited

U.S. PATENT DOCUMENTS

| | | | |
|---|---|---|---|
| 5,418,149 A | 5/1995 | Gelfand et al. | |
| 5,683,896 A | 11/1997 | Hartley et al. | |
| 6,280,998 B1 | 8/2001 | Mathur et al. | |

FOREIGN PATENT DOCUMENTS

| | | |
|---|---|---|
| EP | 1431387 A1 | 6/2004 |
| WO | 9907887 A2 | 2/1999 |
| WO | 0118230 A1 | 3/2001 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Notomi, Tsugunori, et al., "Loop-mediated isothermal amplification of DNA," Nucleic Acids Research, 28(12): e63 (2000) 4 pages.
Mullis, K., et al., "Specific Enzymatic Amplification DNA of In Vitro: The Polymerase Chain Reaction," Cold Spring Harbor Symposium Quant. Biol., 51: 263-273 (1986).
Furrer, B., et al., "Improving PCR efficiency," Nature, 346: 324, (Jul. 26, 1990).
Kunitz, M., "Crystalline Desoxyribonuclease," The Journal of General Physiology, 33: 363-377 (1950).
Yamamoto, M., "Purification and Some Properties of an Acid Deoxyribonuclease From Testes of Chinook Salmon *Oncorhynchus tshawytscha*," Biochim. Biophys. Acta, 228: 95-104 (1971).
Anisimova, Veronika E., et al., "Thermolabile duplex-specific nuclease," Biotechnol. Lett. 31:251-257 (2009).
Anisimova, Veronika E., et al., "Isolation, characterization and molecular cloning of Duplex-Specific Nuclease from the hepatopancreas of the Kamchatka crab," BMC Biochemistry, 9:14-26 (May 21, 2008).
Smith, G.J., et al., "Fast and Accurate Method for Quantitating *E. coli* Host-Cell DNA Contamination in Plasmid DNA Preparations," Biotechniques, 26(3): 518-526 (1999).
Sanyal, Arunik, et al., "An Effective Method of Completely Removing Contaminating Genomic DNA from an RNA Sample to be Used for PCR," Molecular Biotechnology, 8: 135-137 (1997).
Wang, Wen-Yi, et al., "Cloning and characterization of a novel nuclease from shrimp hepatopanceas, and prediction of its active site," Biochem. J., 346: 799-804 (2000).
Corless, C. E., et al., "Contamination and Sensitivity Issues with a Real-Time Universal 16S rRNA PCR," Journal of Clinical Microbiology, 38(5): 1747-1752 (May 2000).
Parida, Manmohan, et al., "Real-Time Reverse Transcription Loop-Mediated Isothermal Amplification for Rapid Detection of West Nile Virus," 42(1): 257-263 (Jan. 2004).
Weidmann, Martin, et al., "Ligase Chain Reaction (LCR)—Overview and Applications," Genome Research, 3: S51-S64 (1994).
Silkie, Sarah S., et al., "Reagent decontamination to eliminate false-positives in *Escherichia coli* qPCR", Journal of Microbiological Methods, 72: 275-282 (2008).
Frey, Bruno, "Protocol: PCR Decontamination with UNG (Uracil DNA Glycosylase)," in PCR Applications Manual by Boehring Mannheim GmbH Biochemica, Chapter 2: Basic PCR: Protocols and Optimization Strategies, pp. 42-43 (1995).
Sobek, H., et al., "Heat-labile uracil-DNA glycosylase: purification and chracterization," FEBS Letters, 388: 1-4 (1996).
Search Report for GB application 0912637.6, dated Nov. 23, 2009.
Notification of Transmittal of IPER, International Search Report and Written Opinion for PCT/GB2010/001384 dated Dec. 6, 2010.

* cited by examiner

*Primary Examiner* — Richard Hutson
(74) *Attorney, Agent, or Firm* — Rothwell, Figg, Ernst & Rothwell, p.c.

(57) ABSTRACT

The invention provides methods of removing nucleic acid contamination from reverse transcription reactions and hot-start PCR, wherein said hot-start PCR is a barrier hot-start PCR set up and/or involves a hot-start DNA polymerase, which methods comprise use of a DNase that is substantially irreversibly inactivated by heating at a temperature of about 50° C. for 5 minutes, and that is substantially specific for double stranded DNA. The invention further provides a DNase that is substantially irreversibly inactivated by heating at a temperature of about 50° C. for 5 minutes, and that is substantially specific for double stranded DNA, nucleic acids encoding said DNase and kits or compositions comprising said DNase or said nucleic acid.

22 Claims, 18 Drawing Sheets

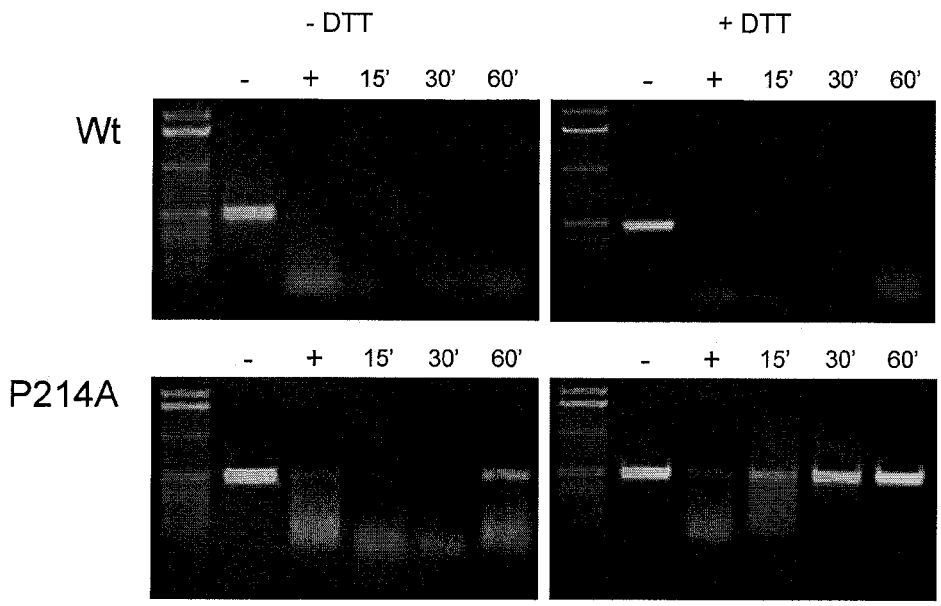
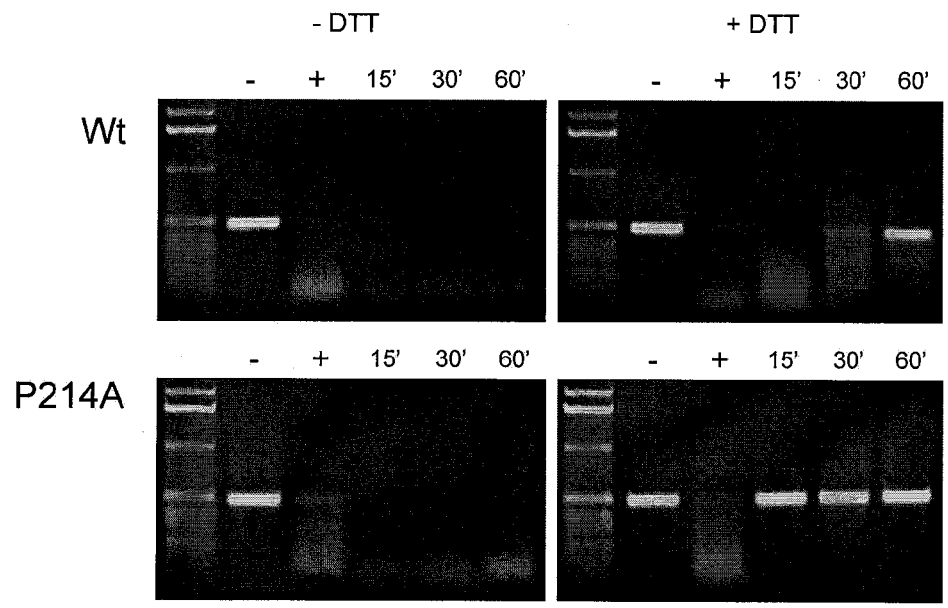
Figure 1a

65 °C
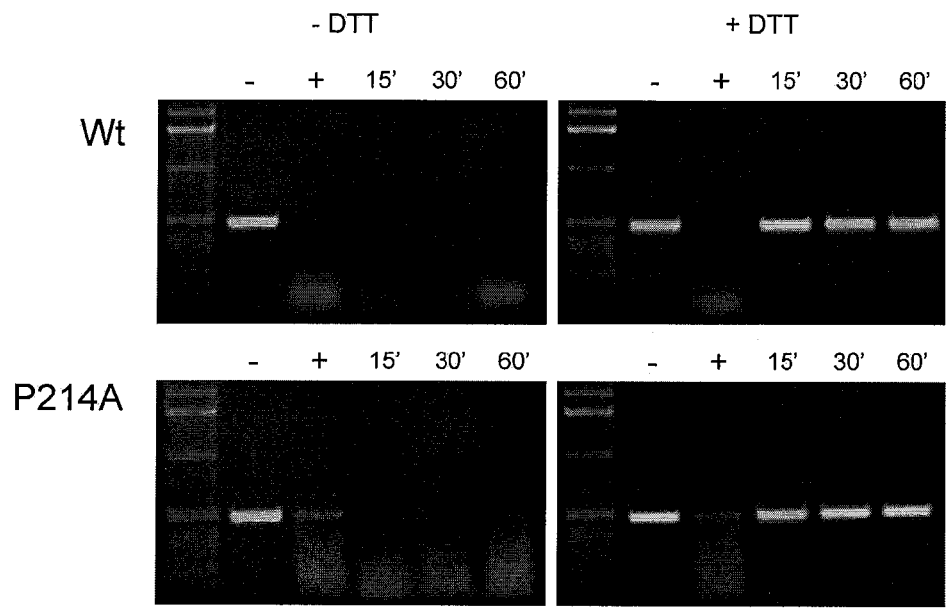
94 °C
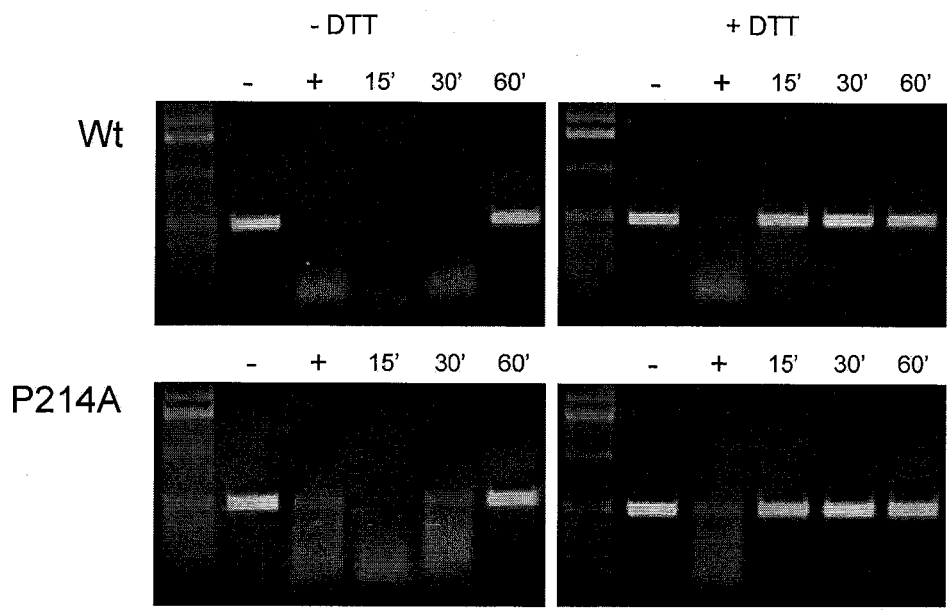
Figure 1b

```
1    EDCVWDNDVDYPEYPPLILDSSFQLVLPVLEGDQRITSVQSGSKLILACPGRGISALGSE
61   DAQATCLGGKLVEVDGKEWNIVELGCTKMASETIHRNLGQCGDQDLGIYEVIGFDLPTTG
121  HFYELIRVCFDPANETTIFSENIVHGASIAAKDIDPGRPSFKTSTGFFSVSMISVYSQRS
181  QLELMKNLLGDDELAATIIDPSEQFYFAKGHMAADADFVTVVEQDATYYYINALPQWQAF
241  NNGNWKYLEYDTRDLAEKHGTDLTVYSGGWGVLELEDINGNPVEIYLGLAQDKKVVPAPA
301  LTWKVIYEKDTNRAAAIVGINNPHITTAPEPLCTDICSSLTWLDFDFGDLVHGYTYCCSV
361  ADLRAAIPNVPDLGDVDILDE
```

Figure 4

```
                        GAGGACTGTGTCTGGGACAATGATGTAGAC
TATCCTGAGTATCCTCCTCTGATCCTGGATTCATCCTTTCAGCTGGTTCTGCCAGTGTTG      181

GAAGGAGACCAAAGGATAACCAGTGTCCAATCTGGGAGTAAGCTGATCTTGGCTTGTCCT      241

GGGAGGGGAATTTCAGCCCTGGGGTCAGAGGATGCACAAGCCACTTGTCTTGGTGGCAAG      301

CTCGTCGAAGTCGATGGCAAAGAATGGAATATAGTCGAACTCGGCTGCACAAAAATGGCA      361

TCTGAAACCATCCATAGAAACCTTGGACAATGTGGTGATCAAGACCTGGGAATTTACGAA      421

GTCATTGGTTTCGACCTTCCAACAACGGGACACTTCTATGAATTGATACGAGTTTGCTTT      481

GACCCGGCAAATGAGACCACTATTTTTTCCGAGAACATCGTTCACGGAGCCAGCATCGCC      541

GCCAAAGACATTGACCCGGGTCGTCCATCTTTCAAAACATCCACTGGGTTCTTCAGTGTA      601

TCGATGATATCTGTCTATTCGCAAAGAAGTCAGCTGGAGCTCATGAAGAACCTCTTAGGA      661

GATGATGAATTAGCTGCGACAATCATCGATCCTTCAGAGCAGTTCTACTTTGCTAAAGGA      721

CATATGGCTGCTGACGCGGACTTTGTGACAGTAGTTGAGCAGGACGCAACATACTATTAC   781

ATCAACGCGTTGCCTCAATGGCAGGCCTTTAACAATGGAAACTGGAAGTACTTGGAATAC      841

GACACCCGTGACCTGGCTGAAAAACATGGCACTGACCTGACCGTCTACAGTGGTGGCTGG      901

GGGGTTCTAGAGCTTGAAGACATCAACGGAAACCCCGTTGAAATCTATCTTGGCCTCGCC      961

CAGGACAAAAAAGTTGTCCCTGCTCCTGCATTAACATGGAAGGTGATCTATGAGAAGGAC     1021

ACTAACCGAGCTGCTGCTATTGTTGGAATAAACAACCCCCACATCACCACGGCACCAGAA     1081

CCTCTTTGTACCGACATCTGCTCCAGCCTCACATGGCTGGACTTTGATTTTGGGGACCTT     1141

GTCCATGGCTACACCTACTGCTGCTCTGTAGCTGATCTCAGGGCAGCCATTCCCAATGTT     1201

CCAGATTTAGGAGACGTTGATATCTTAGACGAATAA
```

Figure 5

```
cagtcagaactgttgaggagcaATGATAGGCCGGACCACTTTCATAGCTTTATTCGTAAAA      61
                     M  I  G  R  T  T  F  I  A  L  F  V  K        13

GTTCTGACTATTTGGAGCTTTACCAAAGGTGAGGACTGTGTCTGGGACAATGATGTAGAC     121
 V  L  T  I  W  S  F  T  K  G  E  D  C  V  W  D  N  D  V  D      33

TATCCTGAGTATCCTCCTCTGATCCTGGATTCATCCTTTCAGCTGGTTCTGCCAGTGTTG    181
 Y  P  E  Y  P  P  L  I  L  D  S  S  F  Q  L  V  L  P  V  L      53

GAAGGAGACCAAAGGATAACCAGTGTCCAATCTGGGAGTAAGCTGATCTTGGCTTGTCCT    241
 E  G  D  Q  R  I  T  S  V  Q  S  G  S  K  L  I  L  A  C  P      73

GGGAGGGGAATTTCAGCCCTGGGGTCAGAGGATGCACAAGCCACTTGTCTTGGTGGCAAG    301
 G  R  G  I  S  A  L  G  S  E  D  A  Q  A  T  C  L  G  G  K      93

CTCGTCGAAGTCGATGGCAAAGAATGGAATATAGTCGAACTCGGCTGCACAAAAATGGCA    361
 L  V  E  V  D  G  K  E  W  N  I  V  E  L  G  C  T  K  M  A     113

TCTGAAACCATCCATAGAAACCTTGGACAATGTGGTGATCAAGACCTGGGAATTTACGAA    421
 S  E  T  I  H  R  N  L  G  Q  C  G  D  Q  D  L  G  I  Y  E     133

GTCATTGGTTTCGACCTTCCAACAACGGGACACTTCTATGAATTGATACGAGTTTGCTTT    481
 V  I  G  F  D  L  P  T  T  G  H  F  Y  E  L  I  R  V  C  F     153

GACCCGGCAAATGAGACCACTATTTTTTCCGAGAACATCGTTCACGGAGCCAGCATCGCC    541
 D  P  A  N  E  T  T  I  F  S  E  N  I  V  H  G  A  S  I  A     173

GCCAAAGACATTGACCCGGGTCGTCCATCTTTCAAAACATCCACTGGGTTCTTCAGTGTA    601
 A  K  D  I  D  P  G  R  P  S  F  K  T  S  T  G  F  F  S  V     193

TCGATGATATCTGTCTATTCGCAAAGAAGTCAGCTGGAGCTCATGAAGAACCTCTTAGGA    661
 S  M  I  S  V  Y  S  Q  R  S  Q  L  E  L  M  K  N  L  L  G     213

GATGATGAATTAGCTGCGACAATCATCGATCCTTCAGAGCAGTTCTACTTTGCTAAAGGA    721
 D  D  E  L  A  A  T  I  I  D  P  S  E  Q  F  Y  F  A  K  G     233

CATATGGCTGCTGACGCGGACTTTGTGACAGTAGTTGAGCAGGACGCAACATACTATTAC    781
 H  M  A  A  D  A  D  F  V  T  V  V  E  Q  D  A  T  Y  Y  Y     253

ATCAACGCGTTGCCTCAATGGCAGGCCTTTAACAATGGAAACTGGAAGTACTTGGAATAC    841
 I  N  A  L  P  Q  W  Q  A  F  N  N  G  N  W  K  Y  L  E  Y     273

GACACCCGTGACCTGGCTGAAAAACATGGCACTGACCTGACCGTCTACAGTGGTGGCTGG    901
 D  T  R  D  L  A  E  K  H  G  T  D  L  T  V  Y  S  G  G  W     293

GGGGTTCTAGAGCTTGAAGACATCAACGGAAACCCCGTTGAAATCTATCTTGGCCTCGCC    961
 G  V  L  E  L  E  D  I  N  G  N  P  V  E  I  Y  L  G  L  A     313

CAGGACAAAAAAGTTGTCCCTGCTCCTGCATTAACATGGAAGGTGATCTATGAGAAGGAC   1021
 Q  D  K  K  V  V  P  A  P  A  L  T  W  K  V  I  Y  E  K  D     333
```

Figure 6a

```
ACTAACCGAGCTGCTGCTATTGTTGGAATAAACAACCCCCACATCACCACGGCACCAGAA      1081
 T   N   R   A   A   A   I   V   G   I   N   N   P   H   I   T   T   A   P   E         353

CCTCTTTGTACCGACATCTGCTCCAGCCTCACATGGCTGGACTTTGATTTTGGGGACCTT      1141
 P   L   C   T   D   I   C   S   S   L   T   W   L   D   F   D   F   G   D   L         373

GTCCATGGCTACACCTACTGCTGCTCTGTAGCTGATCTCAGGGCAGCCATTCCCAATGTT      1201
 V   H   G   Y   T   Y   C   C   S   V   A   D   L   R   A   A   I   P   N   V         393

CCAGATTTAGGAGACGTTGATATCTTAGACGAATAAaagatattcacgtactacaaccat      1261
 P   D   L   G   D   V   D   I   L   D   E   *                                          404 acaaagagagtgattgctgtacctttaactaaaggtctggacctggtaacatgcttatgt      1321
agttaatggtgtcgaggaattcatcaatcagagragaactacttcaaagagggaaaaatt      1381
aatcgcaattttttgttcattacaagtataatacttatcttattacaatttcgagtacgat    1441
tttaaaggatakatccacacacttatgcacaaagtgatcatcaagttatacagtcttcat      1501
taaaacataagcagtcattacggcatgtttcattcagaagttttcaagatattgattgcc      1561
attctcgatttcttgaaagatgtgcacacatgtggagaagaaatgtaaacatcttaaaat      1621
tcatactctggatatccagatattatgcacacaaaatgtcaagtctcctgcctgcttctt      1681
tggaaagatgtgcatatgcacgcacatgtaaccatgagattcacaaaatgtaatcatctc      1741
ttaatcaaaacctaatcagtcattcaaaaaaaaaaaaaaaaaaaaaaaaa              1791
```

Figure 6b

1    EDCVWDNDVDYPEYPPLILDSSFQLVLPVLEGDQRITSVQSGSKLILACPGRGISALGSE

61   DAQATCLGGKLVEVDGKEWNIVELGCTKMASETIHRNLGQCGDQDLGIYEVIGFDLPTTG

121  HFYELIRVCFDPANETTIFSENIVHGASIAAKDIDPGRPSFKTSTGFFSVSMISVYSQRS

181  QLELMKNLLGDDELAATIIDPSEQFYFAKGHMAPDADFVTVVEQDATYYYINALPQWQAF

241  NNGNWKYLEYDTRDLAEKHGTDLTVYSGGWGVLELEDINGNPVEIYLGLAQDKKVVPAPA

301  LTWKVIYEKDTNRAAAIVGINNPHITTAPEPLCTDICSSLTWLDFDFGDLVHGYTYCCSV

361  ADLRAAIPNVPDLGDVDILDE

Figure 7

```
                                          GAGGACTGTGTCTGGGACAATGATGTAGAC
TATCCTGAGTATCCTCCTCTGATCCTGGATTCATCCTTTCAGCTGGTTCTGCCAGTGTTG     181
GAAGGAGACCAAAGGATAACCAGTGTCCAATCTGGGAGTAAGCTGATCTTGGCTTGTCCT     241
GGGAGGGGAATTTCAGCCCTGGGGTCAGAGGATGCACAAGCCACTTGTCTTGGTGGCAAG     301
CTCGTCGAAGTCGATGGCAAAGAATGGAATATAGTCGAACTCGGCTGCACAAAAATGGCA     361
TCTGAAACCATCCATAGAAACCTTGGACAATGTGGTGATCAAGACCTGGGAATTTACGAA     421
GTCATTGGTTTCGACCTTCCAACAACGGGACACTTCTATGAATTGATACGAGTTTGCTTT     481
GACCCGGCAAATGAGACCACTATTTTTTCCGAGAACATCGTTCACGGAGCCAGCATCGCC     541
GCCAAAGACATTGACCCGGGTCGTCCATCTTTCAAAACATCCACTGGGTTCTTCAGTGTA     601
TCGATGATATCTGTCTATTCGCAAAGAAGTCAGCTGGAGCTCATGAAGAACCTCTTAGGA     661
GATGATGAATTAGCTGCGACAATCATCGATCCTTCAGAGCAGTTCTACTTTGCTAAAGGA     721
CATATGGCTCCTGACGCGGACTTTGTGACAGTAGTTGAGCAGGACGCAACATACTATTAC     781
ATCAACGCGTTGCCTCAATGGCAGGCCTTTAACAATGGAAACTGGAAGTACTTGGAATAC     841
GACACCCGTGACCTGGCTGAAAAACATGGCACTGACCTGACCGTCTACAGTGGTGGCTGG     901
GGGGTTCTAGAGCTTGAAGACATCAACGGAAACCCCGTTGAAATCTATCTTGGCCTCGCC     961
CAGGACAAAAAAGTTGTCCCTGCTCCTGCATTAACATGGAAGGTGATCTATGAGAAGGAC    1021
ACTAACCGAGCTGCTGCTATTGTTGGAATAAACAACCCCCACATCACCACGGCACCAGAA    1081
CCTCTTTGTACCGACATCTGCTCCAGCCTCACATGGCTGGACTTTGATTTTGGGGACCTT    1141
GTCCATGGCTACACCTACTGCTGCTCTGTAGCTGATCTCAGGGCAGCCATTCCCAATGTT    1201
CCAGATTTAGGAGACGTTGATATCTTAGACGAATAA
```

Figure 8

```
cagtcagaactgttgaggagcaATGATAGGCCGGACCACTTTCATAGCTTTATTCGTAAAA    61
                      M  I  G  R  T  T  F  I  A  L  F  V  K     13

GTTCTGACTATTTGGAGCTTTACCAAAGGTGAGGACTGTGTCTGGGACAATGATGTAGAC    121
 V  L  T  I  W  S  F  T  K  G  E  D  C  V  W  D  N  D  V  D     33

TATCCTGAGTATCCTCCTCTGATCCTGGATTCATCCTTTCAGCTGGTTCTGCCAGTGTTG    181
 Y  P  E  Y  P  P  L  I  L  D  S  S  F  Q  L  V  L  P  V  L     53

GAAGGAGACCAAAGGATAACCAGTGTCCAATCTGGGAGTAAGCTGATCTTGGCTTGTCCT    241
 E  G  D  Q  R  I  T  S  V  Q  S  G  S  K  L  I  L  A  C  P     73

GGGAGGGGAATTTCAGCCCTGGGGTCAGAGGATGCACAAGCCACTTGTCTTGGTGGCAAG    301
 G  R  G  I  S  A  L  G  S  E  D  A  Q  A  T  C  L  G  G  K     93

CTCGTCGAAGTCGATGGCAAAGAATGGAATATAGTCGAACTCGGCTGCACAAAAATGGCA    361
 L  V  E  V  D  G  K  E  W  N  I  V  E  L  G  C  T  K  M  A    113

TCTGAAACCATCCATAGAAACCTTGGACAATGTGGTGATCAAGACCTGGGAATTTACGAA    421
 S  E  T  I  H  R  N  L  G  Q  C  G  D  Q  D  L  G  I  Y  E    133

GTCATTGGTTTCGACCTTCCAACAACGGGACACTTCTATGAATTGATACGAGTTTGCTTT    481
 V  I  G  F  D  L  P  T  T  G  H  F  Y  E  L  I  R  V  C  F    153

GACCCGGCAAATGAGACCACTATTTTTTCCGAGAACATCGTTCACGGAGCCAGCATCGCC    541
 D  P  A  N  E  T  T  I  F  S  E  N  I  V  H  G  A  S  I  A    173

GCCAAAGACATTGACCCGGGTCGTCCATCTTTCAAAACATCCACTGGGTTCTTCAGTGTA    601
 A  K  D  I  D  P  G  R  P  S  F  K  T  S  T  G  F  F  S  V    193

TCGATGATATCTGTCTATTCGCAAAGAAGTCAGCTGGAGCTCATGAAGAACCTCTTAGGA    661
 S  M  I  S  V  Y  S  Q  R  S  Q  L  E  L  M  K  N  L  L  G    213

GATGATGAATTAGCTGCGACAATCATCGATCCTTCAGAGCAGTTCTACTTTGCTAAAGGA    721
 D  D  E  L  A  A  T  I  I  D  P  S  E  Q  F  Y  F  A  K  G    233

CATATGGCTCCTGACGCGGACTTTGTGACAGTAGTTGAGCAGGACGCAACATACTATTAC    781
 H  M  A  P  D  A  D  F  V  T  V  V  E  Q  D  A  T  Y  Y  Y    253

ATCAACGCGTTGCCTCAATGGCAGGCCTTTAACAATGGAAACTGGAAGTACTTGGAATAC    841
 I  N  A  L  P  Q  W  Q  A  F  N  N  G  N  W  K  Y  L  E  Y    273

GACACCCGTGACCTGGCTGAAAAACATGGCACTGACCTGACCGTCTACAGTGGTGGCTGG    901
 D  T  R  D  L  A  E  K  H  G  T  D  L  T  V  Y  S  G  G  W    293

GGGGTTCTAGAGCTTGAAGACATCAACGGAAACCCCGTTGAAATCTATCTTGGCCTCGCC    961
 G  V  L  E  L  E  D  I  N  G  N  P  V  E  I  Y  L  G  L  A    313

CAGGACAAAAAAGTTGTCCCTGCTCCTGCATTAACATGGAAGGTGATCTATGAGAAGGAC   1021
 Q  D  K  K  V  V  P  A  P  A  L  T  W  K  V  I  Y  E  K  D    333
```

Figure 9a

```
ACTAACCGAGCTGCTGCTATTGTTGGAATAAACAACCCCCACATCACCACGGCACCAGAA    1081
 T  N  R  A  A  A  I  V  G  I  N  N  P  H  I  T  T  A  P  E      353

CCTCTTTGTACCGACATCTGCTCCAGCCTCACATGGCTGGACTTTGATTTTGGGGACCTT    1141
 P  L  C  T  D  I  C  S  S  L  T  W  L  D  F  D  F  G  D  L      373

GTCCATGGCTACACCTACTGCTGCTCTGTAGCTGATCTCAGGGCAGCCATTCCCAATGTT    1201
 V  H  G  Y  T  Y  C  C  S  V  A  D  L  R  A  A  I  P  N  V      393

CCAGATTTAGGAGACGTTGATATCTTAGACGAATAAagatattcacgtactacaaccat    1261
 P  D  L  G  D  V  D  I  L  D  E  *                              404 acaaagagagtgattgctgtacctttaactaaaggtctggacctggtaacatgcttatgt    1321
agttaatggtgtcgaggaattcatcaatcagagragaactacttcaaagagggaaaaatt    1381
aatcgcaatttttgttcattacaagtataatacttatcttattacaatttcgagtacgat    1441
tttaaaggatakatccacacacttatgcacaaagtgatcatcaagttatacagtcttcat    1501
taaaacataagcagtcattacggcatgtttcattcagaagttttcaagatattgattgcc    1561
attctcgatttcttgaaagatgtgcacacatgtggagaagaaatgtaaacatcttaaaat    1621
tcatactctggatatccagatattatgcacacaaaatgtcaagtctcctgcctgcttctt    1681
tggaaagatgtgcatatgcacgcacatgtaaccatgagattcacaaaatgtaatcatctc    1741
ttaatcaaaacctaatcagtcattcaaaaaaaaaaaaaaaaaaaaaaaaaa             1791
```

Figure 9b

```
Arctic Shrimp   1  EDCVWDNDVDYPEYPPLILDSSFQLVLPVLEGDQRITSVQSGSKLILACPGRGISALGSE
King crab      27  QDCVWDKDTDFPEDPPLIFDSNLELIRPVLENGKRIVSVPSGSSLTLACSGSELINLGME
                   *****  *  ** **** **    *  ****   ** **  *** * ***  *     ** *

Arctic         61  DAQATCLGGKLVEVDGKEWNIVELGCTKMASETIHRNLGQCGDQDLGIYEVIGFDLPTTG
King           87  AVEAKCAGGVMLAIEGTEWEIWSLGCSNHVKETIRRNLGTCGEADQGDRHSIGFEYYGGS
                     *  **       *  ** *  *  ***    ***  ****  **   *     ***

Arctic        121  HFYELIRVCFDPANETTIFSENIVHGASIAAKDIDPGRPSFKTSTGFFSVSMISVYSQRS
King          147  IYYELISVCFGPVSETTLRTEHVLHGANIAAKDIETSRPSFKTSTGFFSVSMSTVYSQAS
                    **** ***  * **** * * *  ***  *****  * **********    **** *

Arctic        181  QLELMKNLLGDDELAATIIDPSEQFYFAKGHMAPDADFVTVVEQDATYYYINALPQWQAF
King          207  QLQLMTDILGDSDLANNIIDPSQQLYFAKGHMSPDADFVTVAEQDATYYFINALPQWQAF
                   ** **   ***  **  ****** * ******* ********  ****** **********

Arctic        241  NNGNWKYLEYDTRDLAEKHGTDLTVYSGGWGVLELEDINGNPVEIYLGLAQDKKVVPAPA
King          267  NNGNWKYLEYATRDLAESHGSDLRVYSGGWSLLQLDDINGNPVDILLGLSEGKEVVPVPS
                   ********** ****** ** ** ******   * *******  * ***   * *** *

Arctic        301  LTWKVIYEKDTNRAAAIVGINNPHITTAPEPLCTDICSSLTWLDFDFGDLVHGYTYCCSV
King          327  LTWKVVYEESSSKAAAIVGINNPHITTAPSPLCSDLCSSLTWIDFNLDDLAHGYTYCCAV
                   *****  **    ****************  *** * ******  **    ** ******* *

Arctic        361  ADLRAAIPNVPDLGDVDILDE
King          387  DDLRQAIPYIPDLGNVGLLTN
                     ***  ***  **** *     *
```

Figure 11

METHOD OF REMOVING NUCLEIC ACID CONTAMINATION IN REVERSE TRANSCRIPTION AND AMPLIFICATION REACTIONS

This application claims priority from U.S. Provisional Application 61/235,177, filed Aug. 19, 2009 and GB Application 0912637.6, filed Jul. 21, 2009. These prior applications are incorporated herein by reference.

The present invention relates to the removal of contaminating DNA from reverse transcription reaction mixtures, hot-start DNA polymerase preparations and hot-start PCR reaction mixtures through the use of a DNase. The invention also relates to the prevention of false positive results in nucleic acid amplification reactions through the use of a DNase, in particular amplification reactions which involve reverse transcription of the target sequence, a hot-start DNA polymerase and/or a barrier hot-start PCR set-up. The invention also relates to an extremely thermolabile DNase suitable for use in such methods.

Nucleic acid amplification techniques such as polymerase chain reactions (PCR's) are one of the most powerful tools available in biotechnology, allowing preparation of a large number of copies of a target sequence from a sample containing only a small amount of nucleic acid. In the case of PCR, oligonucleotide primers complementary to their respective strands of a double stranded target sequence are added to the reaction mixture containing the target sequence and free nucleotides. Thermal cycling in the presence of a DNA polymerase results in amplification of the sequence between the primers. The ability of the amplified fragments created by the PCR process to act as templates for subsequent PCR cycles results in the rapid production of a considerable quantity of the target sequence. Even a single copy of the target sequence can yield sufficient nucleic acid to allow detection by, e.g. hybridization with a labelled probe or incorporation of a $^{32}P$ labelled deoxynucleotide triphosphates into the amplified segment.

Ligase amplification reaction (LAR) also known as ligase chain reaction (LCR), like PCR, uses repetitive cycles and alternating temperature to achieve an exponential increase in the number of copies of the target sequence. In this method, DNA ligase catalyses the joining of two oligonucleotides complementary to adjacent regions of one of the target DNA strands. Two other oligonucleotides complementary to the other strand can also be ligated. After denaturation, the original template strands and the two ligated pairs can act as templates for further hybridisation and ligation.

Strand displacement amplification (SDA) exploits the property of the enzymes involved in DNA excision DNA repair to replace a single nicked strand of DNA in a DNA duplex with a newly synthesised strand. To create a nicked single strand repeatedly an endonuclease restriction enzyme, e.g. HindI or BsoBI, is used which only nicks DNA on one strand of its recognition site when the opposite strand is hemiphosphorothiolated. The primers used in this method contain an appropriate recognition site and dATPαS is used in the polymerisation reaction.

Nucleic acid sequence based amplification (NASBA), also known as 3SR (Self-Sustaining Sequence Replication) is essentially an in vitro version of natural retroviral transcription. 3SR involves repetitive reverse transcription from the RNA template to form a cDNA template. From the cDNA template an RNA polymerase produces the corresponding RNA.

Loop-mediated isothermal amplification (LAMP; Notomi, T., et al, Nuc. Acid Res. 2000 Vol 28 (12) e63) is based on the principle of autocycling strand displacement DNA synthesis. A DNA polymerase with a high strand displacement activity is used (e.g. Bst DNA polymerase large fragment) with specifically designed primers. This process involves strand separation to reveal new target sequence without the need for strand melting (the process is therefore isothermal).

Reverse transcription is a process in which a single strand RNA (ssRNA) template is transcribed into a complementary single stranded DNA. The single stranded DNA may then be used to form double strand DNA (dsDNA). Some enzymes are capable of producing the first DNA strand and synthesising the second strand to form dsDNA and others are specific for just one of the two steps. The ssDNA and dsDNA may then be used in a variety of molecular biology applications. For instance they could be used directly in probe based detection assays (e.g. Southern blotting), sequencing experiments or in cloning protocols. Very often the cDNA will be further amplified in an amplification reaction such as PCR, LCR, SDA, LAMP or 3SR, for example to provide more material for the above experiments or to be able to quantify the amount of RNA template present in the original sample.

Reverse transcription linked amplification reactions can be "one step" or "two step" processes. In a one step process the components of the reverse transcription reaction and the nucleic acid amplification reaction are present in a single reaction vessel and typically the early reaction conditions are selected to allow the reverse transcription reaction to proceed to completion and reaction conditions are then switched to conditions suitable to allow the nucleic acid amplification reaction to proceed.

In a two step process the components of the reverse transcription reaction are first combined and the reverse transcription reaction is performed. The reverse transcription product is then combined with the components of the amplification reaction and subjected to the amplification reaction. In a "one tube" two step protocol the amplification reaction components are added to the same reaction vessel in which the reverse transcription reaction was performed. In a "two tube" two step protocol the amplification reaction is performed in a fresh reaction vessel.

Reverse transcription can be combined with any of PCA, LAMP, LCR, SDA or BSR in a one or two step process. In the case of SDA a thermostable strand displacing enzyme and a thermostable restriction enzyme (e.g. BsoB1) should be chosen.

The ability of these amplification techniques to amplify minute quantities of a target sequence makes them highly susceptible to contamination by genomic DNA in the case of RNA target sequences (i.e. those amplification reactions following or using reverse transcription), and by target sequences in DNA molecules from previous amplification reactions, both of which may be carried over in reagents (e.g. the polymerase, the primers, the reaction buffer, etc.), pipetting devices, laboratory surfaces, gloves or aerosolization. Aerosols can occur by disturbing a solution such as during a spill or even by disturbing the small amount of material on a container surface such as the residue on the inner surface of a cap of a plastic tube which can be aerosolized when the tube is opened. When the sample nucleic acid is being investigated for medical diagnostic or forensic reasons, the impact of false-positive results caused by the accidental introduction into the reaction mixture of nucleic acid which may comprise the target sequence, known as carry-over, can be far-reaching.

Amplification reactions of particular susceptibility to the detrimental effects of nucleic acid contamination are the quantitative PCR techniques as these have the power to quantify less than 20 copies of a DNA sequence in a reaction. Thus, even the smallest levels of nucleic acid contamination can give false results in qPCR techniques. In addition, these methods require the detection of signals from the amplified target nucleic acids above an inevitable background signal. Contaminating nucleic acid can contribute to this background signal and so reduce the sensitivity of the technique. As such, minimising contaminating nucleic acid maximises the sensitivity of a quantitative PCR experiment. In experiments where small numbers of copies of target nucleic acids are detected, e.g. quantitative PCR-based pathogen diagnostics and pathogen load quantification, it is paramount that sensitivity of the quantitative PCR is maximised and false positives are minimised. In the field of bacteria identification and diagnostics where segments of highly conserved bacterial DNA are targeted (e.g. 16SrRNA or 23SrRNA genes) by qPCR techniques, nucleic acid contamination arising from the DNA polymerase preparation (which are typically obtained from bacteria and bacterial expression systems) is a major problem. Methods to remove bacterial nucleic acid contaminants efficiently from DNA polymerase preparations are therefore needed. Especially sought are methods that can achieve this without having a detrimental impact on downstream amplification reactions and without damaging the polymerase.

A number of techniques for preventing or limiting the effects of carry-over have been developed. In the case of PCR these include nested primers, primers which anneal to the target sequence inside the annealing boundaries of the two primers used to start PCR (K. B. Mullis et al. Cold Spring Harbour Symposia Vol. LI, pp 263-273, 1986). The shorter PCR amplified product of the nested primers cannot anneal with the starting primers so if it is this product which is carried over, the use of the starting primers will not amplify this carry-over. However, the carry-over has not been removed and if the same nested primers are used in a subsequent PCR, the previously amplified product of the nested primers will be amplified.

Methods have been developed which involve incorporation of the nucleotide deoxyuridine triphosphate (dUTP) into reverse transcribed/amplified nucleic acid sequences in place of deoxythymidine triphosphate (dTTP). As deoxyuridine (dU) is not normally found in naturally-occurring DNA, this base distinguishes previously produced amplicons from new target sequences. Prior to the commencement of further reverse transcription/amplification reactions, the amplification reaction mixture can be treated with the enzyme uracil DNA glycosylase (UNG) which removes the uracil base, leaving the sugar-phosphodiester backbone intact producing an abasic site in single strand (ss) and double strand (ds) DNA (U.S. Pat. No. 5,418,149). The temperature of the amplification reaction mixture is elevated to cleave the DNA at the abasic sites which results in degradation of the carry-over.

This method too is not without problems, as the introduction of dUTP in the reverse transcription/amplification product can interfere with subsequent analysis of the product e.g. by restriction enzyme cleavage or PCR (polymerisation efficiency can be reduced and the use of proof-reading polymerases is precluded). Also, the UNG should be irreversibly inactivated otherwise the products from subsequent reverse transcription/PCR reactions will be degraded. Elevated temperature is a common mechanism to inactivate UNG enzymes, but many of the UNG enzymes commercially available to date are not successfully inactivated even after exposure to the temperatures of a PCR reaction. To minimise the impact of residual UNG activity the temperature steps used in the amplification reaction must be above 54° C. and the reaction vessel must be kept at high temperatures or immediately frozen, to prevent the newly produced amplifications which will also contain uracil from being degraded. Recently a UNG from cod has been described which can be completely irreversibly inactivated when incubated at 50° C. for 10 minutes and this has made UNG based approaches more widely applicable.

However, a further limitation for any UNG system is that it cannot rid the reaction mixture of contaminating genomic DNA since genomic DNA will not have the uracil modification. Accordingly UNG systems are not capable of addressing genomic DNA contamination of reverse transcription reactions.

It has also been suggested that individual PCR reaction mixtures be treated prior to addition of the target DNA and Taq DNA polymerase with DNaseI or restriction endonucleases that cut internal to the target sequence thus preventing amplification of contaminating DNA (Furrer et al. Nature. Vol. 346 page 324, 1990). Similarly, reverse transcription reaction mixtures can be treated in this way prior to addition of the reverse transcriptase. This method requires a decontamination time of 30 minutes and in order to inactivate the DNaseI or restriction endonuclease after decontamination the reaction mixture is boiled. Because of this boiling step, it is necessary to add the DNA polymerase or the reverse transcriptase after decontamination. Of course, this represents a further risk of the introduction of carry-over into the pre-amplification/pre-reverse transcription mixture and decontamination of the DNA polymerase itself is precluded. Primer concentrations of 1 µM must be used in this method because of DNaseI activity towards single stranded DNA.

DNases that are more thermolabile have also been described. WO99/007887 discloses a DNase isolated from *Pandalus borealis* that is substantially irreversibly inactivated after 2 mins at 94° C. This same enzyme is also substantially irreversibly inactivated after 15 minutes at 65° C. Anisimova et al (Biotechnology Letters; 2009, 31: 251 to 257) describe a randomly mutated version of king crab DNase (Kamchatka crab, *Paralithodes camtschaticus*) that is inactivated after incubation for 10 minutes at 65° C., although inactivation can be achieved at temperatures as low as 55° C. after 10 minutes if the inactivation additives DTT (1-4 dithiothreitol) and EDTA are used.

EDTA is a metal ion chelating agent and so can interfere with the action of enzymes that are sensitive to metal ion concentration. Anisimova indicate that the activity of the king crab DNase is positively influenced by $Mg^{2+}$ ions and so EDTA contributes to its inactivation by sequestering this activator. DNA polymerases are also very sensitive to metal ion concentration and, in particular, the $Mg^{2+}$ content of polymerase reaction mixtures must be carefully controlled. As a result, use of EDTA in a DNase inactivation step has the potential to directly inhibit the activity of downstream polymerase reactions. It is therefore preferable not to use EDTA in processing steps preceding a polymerase reaction (e.g. reverse transcription, PCR, SDA, 3SR).

As the mutant king crab DNase provided by Anisimova requires the presence of EDTA to allow inactivation to occur at temperatures below 65° C., this DNase is not suitable for use in a DNA contaminant removal step that precedes a reverse transcription reaction (which are typically performed at around 50° C.). To allow this enzyme to be used without the risk of EDTA inhibition of downstream steps there must be an inactivation step where the mixture is heated to above 65° C. As this is above the typical reverse transcription reaction temperature, this step will be separate and in addition to the reverse transcription step. This adds an additional step to the process thereby increasing the complexity and the labour-intensity of the process and which also, in the field of molecular biology where the process may be repeated many times, represents a significant disadvantage in terms of energy costs and equipment usage times. Moreover, unless the reverse transcriptase is added after the DNase treatment and inactivation, the DNase will be active during the reverse transcription step and so there is the risk that the cDNA product will be degraded. The later addition of the reverse transcriptase to the reaction mixture would represent an opportunity for contamination to occur and a complication to the process as a whole, again with cost implications.

The present inventors have realised that a DNase which can be substantially irreversibly inactivated at temperatures compatible with the step of reverse transcription, and which is substantially specific for double stranded DNA, would provide a highly effective and efficient method. However, there is no DNase currently available with these properties. Such a DNase could be used to decontaminate a complete reverse transcription reaction mixture (i.e. a reaction mixture that contains all of the basic components required for reverse transcription of an RNA molecule to occur) immediately prior to the reverse transcription reaction and then upon initiation of the reverse transcription reaction (i.e. elevation of the temperature of the reaction mixture to the working temperature of the chosen reverse transcription enzyme, e.g. 50° C. or above) the DNase would be substantially irreversibly inactivated over the course of the reverse transcription reaction (with the majority of the inactivation ideally occurring in the first minutes of the reaction). This timecourse of inactivation is important as it means that the newly formed cDNA would not be degraded by the DNase. Unlike a DNase with a higher inactivation temperature, such a DNase would not require a separate inactivation step and/or a later addition of reverse transcriptase.

The present inventors have now produced an enzyme with these unique properties. As with all DNases, the extremely thermolabile DNase of the invention digests DNA by cleaving the phosphodiester links of the sugar phosphate nucleic acid backbone.

Thus, according to the present invention, there is provided a method of removing nucleic acid contamination from a reverse transcription reaction which comprises use of a DNase that is substantially irreversibly inactivated by heating at a temperature of about 50° C. for 5 minutes, and that is substantially specific for double stranded DNA. Preferably these inactivation characteristics are achieved in the absence of EDTA The DNase of the invention is thus used to degrade contaminating double stranded DNA present in the reverse transcription reaction mixture or that is present the individual components thereof. Thereby, contaminating DNA in the reverse transcription product (which could be amplified and thereby give false positive results if the reverse transcription product is so used) may be reduced or avoided and non-specific reverse transcription may also be reduced or avoided.

In particular, the method involves contacting the reverse transcription reaction mixture, or the individual components thereof, with the DNase of the invention under conditions which permit digestion of any double stranded DNA therein and then heating said reaction mixture, or the individual components thereof, to inactivate said DNase. Preferably the reaction mixture is be a complete reaction mixture (i.e. including DNA primers) and preferably the complete reaction mixture is heated at a temperature corresponding to the working temperature of the reverse transcription enzyme contained therein.

In another embodiment the reverse transcription reaction is followed by a nucleic acid amplification reaction (e.g. PCR, LCR, SDA, 3SR, LAMP). Preferably, PCR, LCR or LAMP follow the reverse transcription reaction. In a most preferred embodiment the amplification reaction is PCR.

In another embodiment the reverse transcription reaction and the amplification reaction are performed as a one step process, i.e. the reaction vessel has all of the components for the reverse transcription reaction and the amplification reaction present at the same time. However, two step processes may also be used. In such embodiments, the various components of the reaction and partial reaction mixtures can be treated individually with the DNase of the invention.

Alternatively viewed, this aspect of the invention provides use of a DNase that is substantially irreversibly inactivated by heating at a temperature of about 50° C. for 5 minutes, and that is substantially specific for double stranded DNA, in removing nucleic acid contamination from a reverse transcription reaction, preferably wherein the reverse transcription reaction is followed by a nucleic acid amplification reaction, e.g. reverse transcription-PCR. Preferably these inactivation characteristics of the DNase are achieved in the absence of EDTA As mentioned above, the invention has particular utility in preventing or limiting contamination with genomic DNA and carry-over, and in particular in preventing or reducing false positive results due to carry-over and/or contamination with genomic DNA.

In a further aspect the invention also provides a method of preventing or reducing false positive results due to genomic DNA contamination and/or carry-over in reverse transcription reactions, said method comprising using a DNase that is substantially irreversibly inactivated by heating at a temperature of about 50° C. for 5 minutes, and that is substantially specific for double stranded DNA, to degrade contaminating genomic DNA and/or carried-over double stranded DNA present in the reverse transcriptase reaction mixture or the individual components thereof. Preferably these inactivation characteristics of the DNase are achieved in the absence of EDTA.

The DNase of the invention is also suitable for use in the elimination or reduction of carry-over in all amplification reactions. This is because the lower the inactivation temperature of the DNase the easier it is to inactivate it during the amplification process and the greater the degree of inactivation that can be achieved at any given temperature used in the inactivation step, which can conveniently be the DNA denaturation step (e.g. 94° C. for 5 minutes) for dsDNA amplification protocols.

According to the present invention, there is also provided a method of removing nucleic acid contamination from a nucleic acid amplification reaction which comprises use of the DNase of the invention.

The DNase of the invention is thus used to degrade non-target double stranded DNA present in the amplification reaction mixture or the individual components thereof. Thereby, non-specific amplification may be reduced or avoided.

In particular, the method involves contacting the amplification reaction mixture, or the individual components thereof, with the DNase of the invention under conditions which permit digestion of any double stranded DNA therein; heating said reaction mixture, or the individual components thereof, to inactivate said DNase and thereafter bringing said mixture, or the individual components thereof, into contact with said target nucleic acid to be amplified.

Alternatively viewed, this aspect of the invention provides use of the DNase of the invention in removing nucleic acid contamination from an amplification reaction mixture.

As mentioned above, the invention has particular utility in preventing or limiting carry-over in nucleic acid amplification reactions, and in particular in preventing or reducing false positive results due to carry-over.

In a further aspect the invention also provides a method of preventing or reducing false positive results due to carry-over in nucleic acid amplification reactions, said method comprising using the DNase of the invention to degrade carried-over non-target double stranded DNA present in the amplification reaction mixture, or the individual components thereof.

The DNase of the present invention can also be used to remove nucleic acid contaminants from DNA polymerase preparations as well as being used to remove nucleic acid contaminants from amplification reaction mixtures comprising a DNA polymerase. The low inactivation temperature of the DNase of the present invention means that inactivation of the DNase after decontamination can be achieved without having a, or having a minimal, detrimental impact on the polymerase.

The invention is particularly suited to the removal of nucleic acid contamination from so called hot-start DNA polymerases. Numerous hot-start polymerases have been developed. The objective behind hot-start DNA polymerases is to modify the polymerase to prevent the enzyme from acting as a DNA polymerase (the ability to elongate a primed polynucleotide sequence) until the amplification reaction mixture reaches temperatures approximating the optimum catalytic temperature of the DNA polymerase, or at least temperatures at which primer annealing is sufficiently sequence specific to avoid or minimise non-specific amplification. This is because at lower temperatures primers can anneal non-specifically to the nucleic acid sample and give rise to non specific amplification products which can give false results and/or have inhibitory effects on the reaction. In addition, in some cases the polymerase activity is less accurate and sequence errors can arise in the amplification products. This increased specificity makes hot-start polymerases especially suitable for use in quantitative PCR.

One approach to creating hot-start DNA polymerases is to attach thermolabile groups to the polymerase that, while attached, inhibit or prevent the catalytic action of the polymerase, but which dissociate from the polymerase at temperatures approximating the optimum catalytic temperature of the polymerase, or at least temperatures at which primer annealing is sufficiently sequence specific to avoid or minimise non-specific amplification.

Suitable thermolabile groups include polymerase specific antibodies and affibodies, other specific polymerase binding proteins, specific oligonucleotide aptamers, non specific coatings (e.g. wax), and covalent chemical modifications of the amino acids of the polymerase (e.g. the amino acids in the active site). Decontamination of such polymerases with a DNase that is inactivated above the hot-start activation temperature of the hot-start polymerase would mean that the hot-start properties of the hot-start polymerase could be detrimentally affected. The present invention advantageously permits the removal of DNA contaminants in preparations of hot-start polymerases with a DNase and subsequent inactivation of the DNase at temperatures that are below the hot-start activation temperature of typical hot-start polymerases and thus detrimental impact on the hot-start properties of hot-start polymerases can be avoided.

The hot-start polymerases discussed above are only one approach to performing hot-start PCR. Other approaches prevent one or more of the PCR reaction mixture components from coming into contact with the remaining components. Typically the polymerase or the target nucleic acid is sequestered behind, or in, a material (typically lipid, e.g. a wax) with a melting point at a temperature approximating the optimum catalytic temperature of the polymerase, or at least at a temperature at which primer annealing is sufficiently sequence specific to avoid or minimise non-specific amplification. The DNase of the invention therefore also allows nucleic acid contamination of these so called "barrier" hot-start PCR set ups to be removed without detrimental impact on this type of hot-start PCR.

Thus, the invention provides a method of removing nucleic acid contamination from a hot-start PCR, wherein said reaction is a barrier hot-start PCR set up and/or involves a hot-start DNA polymerase, which method comprises use of the DNase of the invention.

The DNase of the invention is thus used to degrade non-target double stranded DNA present in the hot-start PCR reaction set up/mixture. Thereby, non-specific amplification may be reduced or avoided.

In particular, the method involves contacting the hot-start PCR reaction set up/mixture with the DNase of the invention under conditions which permit digestion of any double stranded DNA therein; heating said reaction set up/mixture to inactivate said DNase and thereafter causing said target nucleic acid to be contacted with the remaining components of the reaction set up/mixture.

Alternatively viewed, this aspect of the invention provides the use of the DNase of the invention in removing nucleic acid contamination from a hot-start PCR reaction, wherein said reaction is a barrier hot-start reaction and/or involves a hot-start polymerase.

The invention also has particular utility in preventing or limiting carry-over in hot-start PCR reactions, wherein said reactions are barrier hot-start reactions and/or involve a hot-start DNA polymerase, and in particular in preventing or reducing false positive results due to carry-over.

In a further aspect the invention also provides a method of preventing or reducing false positive results due to carry-over in hot-start PCR reactions, wherein said reactions are barrier hot-start reactions and/or involve a hot-start DNA polymerase, said method comprising using the DNase of the invention to degrade carried-over non-target double stranded DNA present in the hot-start PCR reaction set up/mixture.

The invention also provides a method of removing nucleic acid contamination from a hot-start DNA polymerase preparation which comprises the use of the DNase of the invention. The use of a DNase of invention in this method is also provided.

The DNase of the invention is thus used to degrade double stranded DNA present in the hot-start DNA polymerase preparation. In particular, the method involves contacting the hot-start DNA polymerase preparation with the DNase of the invention under conditions which permit the digestion of any double stranded DNA present in the DNA polymerase preparation and then heating the preparation to inactivate said DNase.

The present invention also provides a method of in vitro amplification, reverse transcription or hot-start PCR amplification of a target nucleic acid, wherein said hot-start PCR is a barrier hot-start reaction and/or involves a hot-start DNA polymerase, characterised in that said method includes a step of treating the reaction mixture, the reaction set up, or the individual components thereof with the DNase of the invention prior to commencement of the actual amplification or reverse transcription reaction.

"Reverse transcription" is the process by which an RNA-dependent DNA polymerase catalyses the formation of a DNA molecule complementary to an RNA template (cDNA).

More specifically the polymerase catalyses the polymerisation of deoxyribonucleoside triphosphates in a sequence that is complementary (i.e. following Watson-Crick base pairing rules) to a primed template RNA sequence.

Numerous enzymes have been identified that have the ability to catalyse this reaction and examples include, but are not limited to, HIV reverse transcriptase, AMV reverse transcriptase, M-MLV reverse transcriptase, C. therm. polymerase, and Tth polymerase. These enzymes have a range of optimum working temperatures. Those isolated from organisms such as viruses that infect animal hosts have an optimum working temperature of around 37° C. Thermostable reverse transcriptases have however been identified and have also been produced by mutating wild-type reverse transcriptases and it is these thermostable enzymes that are the enzymes that are typically used in reverse transcriptase reactions in the laboratory. At the lower end of the spectrum is AMV with a working range of 42 to 60° C., whereas the reverse transcriptase activity of Tth DNA polymerase and C. therm. DNA polymerase have working ranges of 55 to 70° C. and 60 to 70° C. respectively.

At its most basic a complete reverse transcription reaction mixture will contain a reverse transcription enzyme, an RNA template, suitable primers that can bind to the template and from which the reverse transcriptase can begin polymerisation, dNTP's and a suitable buffer. Incubation of the mixture at the working temperature of the reverse transcriptase results in cDNA production. Upon completion of the reverse transcription reaction the cDNA can be used directly in sequencing or genotyping experiments or maybe in cloning or detection protocols.

By "reverse transcription enzyme" it is meant any enzyme that has reverse transcriptase activity (i.e. the ability to catalyse the polymerisation of a complementary DNA counterpart to a primed RNA template sequence or RNA dependent DNA polymerase activity). This activity may be the sole activity of the enzyme or, more typically, may be a component activity of an enzyme (e.g. HIV reverse transcriptase, M-MLV reverse transcriptase, AMV reverse transcriptase, Tth DNA polymerase, C. therm. polymerase). Typical additional activities the polymerase may have include RNaseH, DNA directed DNA polymerase, DNA-RNA unwinding activity, $Mn^{2+}$ dependent endonuclease. Preferably however RNaseH and/or endonuclease activity will be minimal or absent.

A "reverse transcription enzyme preparation" is any material, typically a solution, generally aqueous, comprising a reverse transcription enzyme. In particular, it refers to commercially prepared preparations of a reverse transcription enzyme, i.e. a reverse transcription enzyme reagent that may be supplied by a commercial supplier of laboratory enzymes, although diluted, adjusted and/or modified versions of such preparations are also encompassed by this term. The reverse transcription enzyme preparation may also be a preparation of a reverse transcription enzyme that has been obtained from a bacterial source which expresses the reverse transcription enzyme naturally and/or that comprises an expression cassette encoding reverse transcription enzyme. The preparation may be purified to an extent as compared with the initial reverse transcription enzyme preparation taken directly from the bacterial source.

The term "nucleic acid amplification reaction" refers to any in vitro means for increasing the number of copies of a target sequence of nucleic acid. Preferably, methods will involve "thermal cycling", i.e. involving high temperature cycling. Amplification methods include, but are not limited to, PCR and modifications thereto, 3SR, SDA, LAR or LCR and LAMP and modifications thereto. PCR, LAMP and LCR and their modifications are thermal cycling methods. Methods may result in a linear or exponential increase in the number of copies of the target sequence. "Modifications" encompass, but are not limited to, real-time amplification, quantitative and semi-quantitative amplification, competitive amplification, and so on.

The target nucleic acid may be DNA or RNA depending on the selected amplification method. For example, for PCR the target is DNA, although when combined with a reverse transcription step the target can be considered to be an RNA sequence. 3SR amplifies RNA target sequences directly.

The term "amplification/reverse transcription reaction mixture" refers to any solution, generally aqueous, comprising the various reagents used to amplify/reverse transcribe a target nucleic acid. These include enzymes, aqueous buffers, salts and nucleoside triphosphates. The term refers to mixtures which contain all the necessary components for carrying out a successful amplification reaction and to mixtures which are incomplete and therefore contain only some (e.g. at least 2, 3 or 4) of the required components. If prefaced by the term "complete" the reaction mixture contains all of the components necessary for reverse transcription and/or amplification.

A "hot-start DNA polymerase" is a DNA polymerase that has been modified, typically by the addition of thermolabile molecular entities, to increase the temperature at which it can perform detectable polymerisation of a primed DNA polynucleotide. The temperature at which the hot-start DNA polymerase can perform detectable levels of DNA polymerisation preferably approximates the optimum catalytic temperature of the polymerase.

The term "hot-start DNA polymerase preparation" refers to any material, typically a solution, generally aqueous, comprising a hot-start DNA polymerase. In particular, it refers to commercially prepared preparations of hot-start DNA polymerase, i.e. a hot-start DNA polymerase reagent that may be supplied by a commercial supplier of laboratory enzymes, although diluted, adjusted and/or modified versions of such preparations are also encompassed by this term. The hot-start DNA polymerase preparation may also be a preparation of a hot-start DNA polymerase that has been obtained from a bacterial source which expresses the polymerase naturally and/or that comprises an expression cassette encoding the polymerase. The preparation may be purified to an extent as compared with the initial polymerase preparation taken directly from the bacterial source. Typically the preparation will have also been treated to apply hot-start blocking entities to the polymerase.

A "hot-start PCR reaction" is a PCR amplification reaction in which detectable polymerisation from a primed DNA polynucleotide only occurs at a temperature approximating the optimum catalytic temperature of the polymerase. Preferred temperatures of detectable polymerisation should be construed consistently with the discussion of hot-start DNA polymerases.

A "hot-start PCR mixture" is a PCR reaction mixture as defined above comprising a hot-start polymerase.

A "barrier hot-start PCR set up" is a reaction vessel comprising two or more components of a PCR reaction mixture wherein at least one component is sequestered from the other component(s) behind, or in, a material with a melting temperature corresponding to temperatures of detectable DNA polymerisation as defined above. Preferably the material is a lipid, e.g. a wax.

By "contamination" is meant the presence in the reaction mixture of nucleic acid that can function as a template for reverse transcription and/or amplification that is not a part of the nucleic acid population that is being targeted for reverse transcription/amplification. The primers being used in the reaction mixture are not contaminants.

The term "removing nucleic acid contamination" is intended to cover both the prevention and reduction of nucleic acid contamination.

The term "carry over" is used to describe any nucleic acid which is accidentally or unintentionally introduced into a reaction mixture, in particular target sequences carried over from previous amplification or reverse transcription reactions.

The term "false positive result" refers to a result which appears to show that the nucleic acid sample under investigation contains the target sequence but wherein the amplified product is derived from carry-over and/or in the case of reverse transcription based amplification reactions, possibly genomic DNA. Clearly, the reduction in false positive results which the invention provides is particularly advantageous in the forensic and diagnostic fields. The methods of the invention enable the specificity of nucleic acid amplification to be increased.

The term "DNase" refers to an enzyme which hydrolyzes a phosphodiester bond in the DNA backbone and is not nucleotide sequence specific.

By "substantially irreversibly inactivated" is meant that on heating, the enzyme is at least 95% inactivated, preferably 98% inactivated, more preferably the enzyme is 100% inactivated. Percentage inactivation can be conveniently measured by incubating a DNA sample (e.g. 500 bp PCR product) for 3 hr either with an inactivated DNase or with a non-inactivated DNase in a suitable buffer (e.g. Tris, HEPES, PBS) at 37° C.; separating the reaction products on an ethidium bromide agarose gel by electrophoresis and measuring the relative intensities of fluorescence of the DNA bands under UV light (Example 2). Alternative methods could be devised by the skilled man to measure to relative activities of inactivated and non-inactivated DNase. For instance, relative changes in fluorescence of SYBR green containing DNA samples could be used. Further methods are the Kunitz assay (Kunitz, M; 1950, S. Gen Physiol, 33:363 and Example 1 and the modified Kunitz assay devised by Yamamoto (Yamamoto, M; 1971, Biochim Biophys Acta, 228:95 and Example 4).

Even when the temperature of the reaction mixture returns to room temperature, the DNase does not regain its activity and there is substantially no residual activity; specifically, less than 5%, preferably less than 2%, most preferably no detectable DNase activity remains.

Substantially irreversible inactivation preferably occurs within 5 minutes of incubation at a temperature of at or about 50° C., e.g. 48 to 52° C. For example in 1, 2 or 3 minutes incubation at 50° C. The DNase of the invention may be substantially irreversibly inactivated at lower temperatures or over shorter time periods but, in accordance with the invention, heating for 5 minutes at about 50° C. must be sufficient to substantially irreversibly inactivate the enzyme. It will be readily apparent to the skilled man that adjustments to one of these two parameters can be compensated for by adjusting the other. For instance increasing the inactivation temperature might permit the duration of incubation to be reduced. Conversely, increasing the duration of incubation might permit a lower inactivation temperature to be used. For example, a DNase in accordance with the invention could be inactivated in a 1 or 2 minute incubation at a temperature of 55° C., in a 3 minute incubation at a temperature of 52° C., in a 4 minute incubation at a temperature of 51° C. in a 10 minute incubation at a temperature of 49° C., or in a 15 minute incubation at a temperature of 48° C. Of course, as is also readily apparent to the skilled man and shown in the Examples, when the DNase of the invention is used in the methods of the invention, durations of incubation longer than five minutes may be used and inactivation temperatures greater than about 50° C. may be used, if practical (e.g. inactivation could take place at each of 50° C., 55° C., 65° C. or 94° C. for each of 15, 30 or 60 minutes; 60° C. for 15 minutes; or 95° C. for 10 minutes). However, to be in accordance with the invention, a DNase must show substantial inactivation if incubated at a temperature of at or about 50° C. for 5 minutes.

Inactivation temperatures and times for a DNase should be assessed by incubating the DNase in a solution that mimics a typical PCR or reverse transcriptase buffer (e.g. 25 mM Tris/HCl, pH 8.5, 5 mM $MgCl_2$). EDTA should preferably be absent. The DNase should be present at about between 0.01 U/μl and 10 U/μl, preferably between 0.05 and 5 U/μl, e.g. 0.5 and 1.5 U/μl.

Inactivation at any given temperature can be enhanced in terms of extent and/or speed by the presence of a disulphide bond reducing agent (i.e. an agent that inhibits and/or disrupts disulphide bonds between two or more cysteine residues in a protein) in the inactivation buffer. Examples of such agents include, but are not limited to DTT, 2-mercaptoethanol, 2-mercaptoethylamine.HCl, TCEP.HCl (Tris(2-Carboxyethyl) phosphine hydrochloride), N-ethylmaleimide. DTT is preferred. Alternatively the disulphide bond reducing agent (e.g. DTT) can be used to reduce the inactivation temperature that is required for a particular duration of inactivation step. The skilled man would be able to determine appropriate concentrations of disulphide bond reducing agent for his needs that would improve inactivation but would not be detrimental to his downstream reactions. For instance, DTT can conveniently be incorporated into the inactivation step at a concentration of between 0.05 and 50 mM. DTT is routinely used in reverse transcription reactions at concentrations of between 1 and 10 mM and is often used in PCR reactions.

Preferably, inactivation of the DNase in the methods of the invention occurs at a DTT concentration of between 0.1 and 10 mM, preferably between 0.5 and 5 mM and most preferably between 1 and 2 mM. For the standard assessment of inactivation temperature a buffer of 25 mM Tris/HCl, pH 8.5, 5 mM $MgCl_2$ and 1 mM DTT is preferably used.

Linear double stranded DNA and supercoiled circular DNA are both substrates of the enzyme according to the invention. The enzyme has little, negligible, or essentially no detectable activity for single stranded DNA such as amplification/reverse transcriptase primers. In other words, the DNase is substantially specific for double stranded DNA.

By "substantially specific for double stranded DNA" it is meant that the DNase cleaves double stranded DNA but has little, negligible or essentially no detectable activity towards single stranded DNA at concentrations of 0.01 to 0.05 U/μl. Preferably, there will be no detectable activity towards single stranded DNA at such concentrations. The skilled man would easily be able to devise an experiment to make a comparison of relative DNase activity towards single and double stranded DNA. Anisimova et al (BMC Biochemistry, 2008, 9:14) disclose such an experiment. Briefly, 2 Kunitz units of a DNase under test were incubated with M13 phage DNA (single stranded) or lambda phage DNA (double stranded) in 50 mM Tris-HCl, pH7.5, 5 mM $MgCl_2$ (30 μl final reaction volume) for one hour and the products were separated on an ethidium bromide agarose gel. Activity against single strand and/or double stranded DNA was observable by the position of the bands relative to untreated controls. Another approach is described in more detail in Example 6. In this approach, the specificity for double- and single stranded DNA of a DNase may be tested by measuring the increase in fluorescence from oligonucleotides labelled with the fluorophore FAM (fluorescein) at the 5' terminus and with TAMRA at the 3' terminus. The emitted light from FAM is absorbed (quenched) by TAMRA when the two labels are in proximity. The cleavage of the oligonucleotide by the DNase results in the separation of FAM from TAMRA and an increase in fluorescence from FAM that can be measured in a fluorimeter with excitation wavelength 485 nm and emission wavelength 520 nm. A double stranded DNA substrate can be prepared by mixing the labelled oligonucleotide with a second oligonucleotide that is complementary to the labelled oligonucleotide. Of course other suitable fluorophore pairs may similarly be used.

In the case of reverse transcription reactions, these characteristics permit the inclusion of the DNase within a reverse transcription reaction mixture comprising the RNA sample, primers, nucleotides, reverse transcriptase and buffers (i.e. a complete reaction mixture) and the rapid degradation of carry-over material and genomic DNA, e.g. at room temperature. These characteristics also allow the inclusion of the DNase in a complete one step reverse transcription based amplification reaction mixture.

These characteristics also allow the inclusion of the DNase in an amplification reaction mixture comprising primers, nucleotides, DNA polymerase and buffers and the rapid degradation of carry over material, e; g. at room temperature.

Advantageously, the thermolabile DNase of the invention is fully functional in a complete amplification reaction mixture, and is compatible with standard in vitro amplification reactants and conditions. The enzyme should also be capable of removing suitable amounts of contaminating genomic DNA and/or carry-over from a reaction mixture, usually fg- or pg-levels but preferably up to 1 ng. Preferably, the DNase is able to degrade all the carry-over within 5 minutes at room temperature, more preferably within 3 minutes, most preferably within 2 minutes.

Raising the temperature of the reaction mixture to the inactivation temperature of the DNase of the invention (around 50° C.) for a short time (e.g. 5 minutes) irreversibly inactivates the DNase of invention.

In the case of reverse transcription reactions, this can conveniently be concomitant with the reverse transcription step. In the case of DNA amplification reactions (including hot-start PCR), the nucleic acid samples to be amplified and analysed (i.e. the target nucleic acid) can then be added and amplification begun. Even when the temperature of the reaction mixture drops during the thermal cycling and after amplification or reverse transcription, the copies of the target sequence will not be degraded because the DNase has been irreversibly inactivated. It is a particular advantage of the present invention that the reverse transcriptase and/or DNA polymerase can be included in the reverse transcription and/or amplification reaction mixtures while the decontamination and subsequent inactivation steps take place. This is as a result of the gentle conditions which result in inactivation of the DNase (about 50° C. for 5 minutes) so a further potential source of contamination is removed.

Preferably the DNase has minimal nuclease activity towards the DNA strand of a DNA:RNA duplex. By "minimal" it is meant that the DNase has a nuclease activity towards the DNA strand of a DNA:RNA duplex that is less than 40% of its activity towards a double stranded DNA. Preferably the DNase will have an activity toward DNA:RNA duplexes that is less than 30% or less than 20% of its activity towards double stranded DNA.

It is these particular characteristics of the preferred DNases of the invention (i.e. rapid substantially irreversible inactivation, double strand specificity and, preferably, minimal DNA:RNA duplex nuclease activity) that make these DNases exceptionally suitable for the decontamination of one step reverse transcription amplification protocols. This is because the entire reaction mixture can be decontaminated, without fear of unwanted degradation of the amplification or reverse transcription products, in a single step and no addition of further materials is required. This minimises contamination risk (including that of genomic DNA) without sacrificing sensitivity through unwanted digestion of the initial reverse transcription product and/or the amplification product.

The DNase enzyme used in the above methods itself constitutes a further aspect of the invention. This aspect of the invention thus provides a DNase that is substantially irreversibly inactivated by heating at a temperature of about 50° C. for 5 minutes and that is substantially specific for double stranded DNA. Preferably these inactivation characteristics are achieved in the absence of EDTA).

Although it is clear that any thermolabile DNase having the characteristics described above may be suitable for use in the methods according to the invention, modified DNases derived from the DNase of *Pandalus borealis*, or a similar DNase from another, preferably marine, organism, in which a particular proline residue has been modified, deleted or substituted form another aspect of the present invention. The organism may be a prokaryote or a eukaryote. By "prokaryote" it is meant any organism that lacks a cell nucleus, i.e. any organism from the domains Bacteria and Archaea. Preferably the organism is a bacterium. More preferably the organism is a eukaryote, e.g. an organism classified in the taxonomic kingdoms Animalia, Plantae, Fungi or Protista, e.g. an organism in the phyla/division Acanthocephala, Acoelomorpha, Annelida, Arthropoda, Brachiopoda, Bryozoa, Chaetognatha, Chordata, Cnidaria, Ctenophora, Cycliophora, Echinodermata, Echiura, Entoprocta, Gastrotricha, Gnathostomulida, Hemichordata, Kinorhyncha, Loricifera, Micrognathozoa, Mollusca, Nematoda, Nematomorpha, Nemertea, Onychophora, Orthonectida, Phoronida, Placozoa, Platyhelminthes, Porifera, Priapulida, Rhombozoa, Rotifera, Sipuncula, Xenoturbellida, Anthocerotophyta, Bryophyta, Marchantiophyta, Lycopodiophyta, Pteridophyta, Pteridospermatophyta, Coniferophyta, Cycadophyta, Ginkgophyta, Gnetophyta, Anthophyta (or Magnoliophyta), Chytridiomycota, Deuteromycota, Zygomycota, Glomeromycota, Ascomycota or Basidiomycota. Organisms from the kingdom Animalia, e.g. invertebrates and vertebrates, are of note. More preferably the organism is selected from those in the phylum Arthropoda, e.g. an organism in the subphylums Crustacea, Hexpoda, Chelicerata or Myriapoda, e.g. an organism in the classes of Crustacea of Branchiopoda, Remipedia, Cephalocarida, Maxillopoda, Ostracoda or Malacostraca, preferably Malacostraca and more preferably an organism in the order Decapoda. The organism may be classified in the family Pandalidae, e.g. in the genera *Anachlorocurtis, Atlantopandalus, Austropandalus, Calipandalus, Chelonika, Chlorocurtis, Chlorotocella, Chlorotocus, Dichelopandalus, Dorodotes, Heterocarpus, Miropandalus, Notopandalus, Pandalina, Pandalopsis, Pandalus, Pantomus, Peripandalus, Plesionika, Procletes, Pseudopandalus* or *Stylopandalus*; the family Lithodidae, e.g. in the genera *Cryptolithodes, Glyptolithodes, Lithodes, Lopholithodes, Neolithodes, Paralithodes, Paralomis, Phyllolithodes* or *Rhinolithode*; or the family Penaeidae, e.g. in the genera: *Farfantepenaeus, Fenneropenaeus, Litopenaeus* or *Marsupenaeus*. The organism is preferably an organism that has evolved to inhabit cold environments, e.g. cold marine or aquatic environments. The organism will preferably be selected from e.g. *Paralithodes camtschaticus* (king crab), *Marsupenaeus japonicus* (kuruma shrimp) or *Penaeus japonicus*. In other embodiments the DNase is from a species of organism that is not a prokaryote, e.g. not a bacterium, e.g. not a psychrotrophic bacterium.

Also included within the scope of the present invention are enzymatically active fragments of these modified DNases.

Thus in a further aspect, the invention provides a DNase or an enzymatically active fragment thereof, said DNase having the sequence of SEQ ID No. 1 or a sequence which is at least 60%, preferably at least 70%, 80%, 90% or 95%, e.g. at least 98%, identical thereto, but wherein the proline residue at position 237 of SEQ ID No 1, or the equivalent proline in other sequences, has been modified, deleted or substituted, said DNase or enzymatically active fragment thereof being substantially irreversibly inactivated by heating at a temperature of about 50° C. for 5 mins, and which is substantially specific for double stranded DNA.

SEQ ID NO:1 is the amino acid sequence of the translated portion of the cDNA for *Pandalus borealis* DNase. The cDNA sequence is shown in SEQ ID NO:2. SEQ ID NO:1 comprises a signal peptide sequence of MIGRTTFIALFVKVLTIWSFTKG (SEQ ID NO:9). The mature form of *Pandalus borealis* DNase is shown in SEQ ID NO:5 (i.e. the sequence of SEQ ID NO:1 without the signal peptide (SEQ ID NO:9). Therefore the proline at residue 237 of SEQ ID NO:1 is the same position as the proline at residue 214 of SEQ ID NO:5.

Thus the invention also provides a DNase or an enzymatically active fragment thereof, said DNase having the sequence of SEQ ID No. 5 or a sequence which is at least 60%, preferably at least 70%, 80%, 90% or 95%, e.g. at least 98%, identical thereto, but wherein the proline residue at position 214 of SEQ ID No 5, or the equivalent proline in other sequences, has been modified, deleted or substituted, said DNase or enzymatically active fragment thereof being substantially irreversibly inactivated by heating at a temperature of about 50° C. for 5 mins, and which is substantially specific for double stranded DNA.

Enzymatically active fragments and variants of SEQ ID No. 1 display at least 70%, preferably at least 85%, more preferably at least 95% and most preferably at least 99% of the enzymatic function of the mature enzyme of SEQ ID No. 5 (i.e. the ability hydrolyse a phosphodiester bond in a DNA backbone without nucleotide sequence specificity). As discussed elsewhere, the activity of a DNase can be assessed easily using routine techniques.

Percentage sequence identity according to the invention can be calculated using any of the widely available algorithms (e.g. using the Clustal W2 multiple sequence alignment program (http://www.ebi.ac.uk/Tools/clustalW2) using default parameters (DNA Gap Open Penalty=15.0; DNA Gap Extension Penalty=6.66; DNA Matrix=Identity; Protein Gap Open Penalty=10.0; Protein Gap Extension Penalty=0.2; Protein matrix=Gonnet; Protein/DNA ENDGAP=-1; Protein/DNA GAPDIST=4)

"Equivalent proline residues in other sequences" than SEQ ID No. 1 or 5 can be readily identified by using standard sequence alignment techniques such as Clustal W2 to produce alignments such as that represented in FIG. 11.

Preferably the DNase of the invention or fragment thereof will have the sequence of a DNase obtainable from a species classified in any of the taxonomic groupings mentioned above, e.g. from the phylum Arthropoda or the subphylums Crustacea, Hexpoda, Chelicerata and Myriapoda, e.g. *Pandalus borealis, Paralithodes camtschaticus* (king crab), *Marsupenaeus japonicus* (kuruma shrimp) or *Penaeus japonicus* but wherein the proline residue equivalent to the proline at position 237 of SEQ ID No 1 has been modified, deleted or substituted. The DNase from *Pandalus borealis* wherein the proline residue equivalent the proline at position 237 of SEQ ID No 1 has been modified, deleted or substituted is preferred.

In a most preferred embodiment the DNase of the invention has the amino acid sequence of SEQ ID NO:3 or 7.

By "substitution" of the proline (e.g. at residue 237 of SEQ ID NO:1/residue 214 of SEQ ID NO:5) it is meant that the proline residue is replaced by another naturally occurring amino acid, typically genetically encoded, or an amino acid analogue. Preferably the proline is replaced by alanine, glycine, serine or cysteine.

By "modification" of the proline it is meant that the proline residue has had its usual stereochemical properties altered, e.g. by replacing its side chain with a different group, modifying the composition of the side chain itself or replacing the hydrogen opposite the side chain with a different side group.

The invention also provides nucleic acid molecules encoding the DNases of the invention. Nucleotide sequences corresponding to the amino acid sequences of SEQ ID NOs: 3 and 7 are disclosed in SEQ ID NOs: 4 and 8. Degeneracy of the genetic code means that SEQ ID NOs:4 and 8 are only two of many possible nucleotide sequences.

The invention also provides the use of the particular DNases described above as a decontaminating agent in methods of amplifying of a nucleic acid. The use of the particular DNases described above in the decontamination methods described herein represents a particularly preferred embodiment of the invention.

A method for the isolation and purification of a DNase or an enzymatically active fragment thereof as described above represents a further aspect of the present invention. Thus, in this aspect the invention provides such a method, said method comprising expressing said DNase or fragment thereof in a suitable host cell (e.g. *Pichia pastoris; E. coli; S. cereviciae*, baculovirus infected insect cells), and subsequently separating the DNase from said host cells and/or the media in which said cells have been cultured. Expression of said DNase or fragment thereof can be achieved by incorporating into a suitable host cell an expression vector encoding said DNase or fragment thereof, e.g. an expression vector comprising a nucleic acid molecule encoding the amino acid sequences of SEQ ID NOs: 3 and 7, for instance nucleic acid molecule comprising the nucleotide sequences of SEQ ID NOs: 4 or 8. Host cells comprising these expression cassettes and nucleic acid molecules are encompassed by the invention.

The DNase enzyme may be separated, or isolated, from the host cells/culture media using any of the purification techniques for protein known in the art and widely described in the literature or any combination thereof. Such techniques may include for example, precipitation, ultrafiltration, dialysis, various chromatographic techniques, e.g. gel filtration, ion-exchange chromatography, affinity chromatography, electrophoresis, centrifugation etc.

Likewise an extract of host cells may also be prepared using techniques well known in the art, e.g. homogenisation, freeze-thawing etc and from this extract the DNase of the invention can be purified.

It has been found that a purification protocol based on a combination of ion exchange chromatography and affinity chromatography, e.g. on a sepharose column, e.g. a Red sepharose (Pharmacia Biotech, Sweden) or a Blue sepharose (GE Healthcare) column, may readily be used to isolate the enzyme.

More particularly, the extract may be subjected to ion-exchange chromatography and the protein eluted with a NaCl gradient. The fractions containing DNase activity may be dialysed and then applied to an affinity column before final elution with NaCl.

The present invention also provides kits which comprise at least a DNase according to the invention. The kits may also contain some or all of the necessary reagents, buffers, enzymes etc. to carry out nucleic acid amplification and/or reverse transcription reactions. More particularly, the kits may contain nucleotide triphosphates (including dNTPαS for SDA), oligonucleotide primers, reverse transcriptases, preferably those capable of functioning at about 50° C., DNA polymerases, preferably a thermostable polymerase such as Taq polymerase or Bst polymerase (and hot-start versions thereof) or, in the case of LAR, a DNA ligase (preferably a thermostable DNA ligase such as Ampligase® or that disclosed in U.S. Pat. No. 6,280,998 which is isolated from *Pyrococcus furiosus*) or a restriction enzyme (preferably a thermostable restriction enzyme such as BsoB1). The DNase may be provided in one compartment together with a reverse transcriptase, DNA polymerase, strand displacement polymerase or LCR ligase.

The present invention also provides compositions comprising a DNase of the invention and one or more of the necessary reagents to carry out nucleic acid amplification and/or reverse transcription reactions and methods, e.g. those components described above. Typically such compositions will be aqueous and buffered with a standard buffer such as Tris, HEPES, etc.

Reverse transcription methods are of course now standard in the art, and may be effected using any known or standard reagents and techniques.

In a typical reverse transcription protocol, the decontamination step may simply involve incubating the reverse transcription reaction mixture containing the DNase for a short period of time, for example 1 to 30 minutes at room temperature, conveniently 2 to 15 minutes. The time of this incubation is not critical and may vary depending on the exact DNase and concentration used, and the other components of the reaction system. The temperature may be any temperature at which the enzyme is active i.e. below the inactivation temperature (e.g. 37° C.), but room temperature is convenient.

Such a reaction mixture may, as mentioned above, contain all the necessary reactants for the reverse transcription reaction.

A typical representative reverse transcription mixture may for example include:

| Component | Final Concentration |
| --- | --- |
| dATP | 50-200 µM |
| dCTP | 50-200 µM |
| dGTP | 50-200 µM |
| dTTP | 50-200 µM |
| Primer | 0.05-0.2 µM |
| AMV reverse transcriptase | 10-200 Units |
| ds DNase of SEQ ID NO:7 | 0.1-2 Units |
| Reverse transcription buffer | 1X |
| Sterile distilled water | to final 50-100 µl |
| Experimental template | 50 pg-100 ng |
| Total Mix | 25-50 µl |

In the above representative example, any combination of sterile distilled water and experimental template volumes can be used as long as the total volume of the reaction (including buffer, dNTPs, primers, enzymes and MgCl$_2$ solutions) equals 50-100 µl. However, alternative final volumes may be used according to choice, to achieve e.g. similar or other desired final concentrations of reactants. Any convenient or commercially available reverse transcription buffer may be used. A suitable 5× reverse transcription buffer may be 250 mM Tris-HCl (pH 8.5 at 25° C.), 40 mM MgCl$_2$, 150 mM KCl, 5 mM DTT. A reverse transcription buffer may be purchased from Fermentas.

Depending on the level of potential contamination, the amount of DNase needed may vary. With a short incubation step (0-15 minutes at room temperature), 2.0 Units/50 µl reaction mixture is generally more than sufficient. 0.1 to 2.0 units/50 µl reaction mixture is suitable and an activity of approximately 0.5 units/50 µl reaction mixture e.g. 0.2 to 1.0 Units/50 µl reaction mixture) is preferred. At a concentration of 2.0 Unit/50µl reaction mixture some ssDNase activity is observed and therefore the activities listed above are preferred. One unit of enzyme is defined as the amount that in the Kunitz assay or the modified Kunitz assay of Yamamoto (both supra) increases the absorption at 260 nm by 0.001 per minute. After incubation, the DNase is inactivated by heating the reaction mixture. Conveniently this may be achieved by heating in the reverse transcription step, e.g. around 50° C. for 30 minutes.

Conveniently the amplification method comprising the decontamination step using a DNase of the invention will involve or be based on the PCR. PCR methods are standard in the art and may be effected using any known or standard reagents and techniques.

In a typical PCR reaction protocol, the decontamination step may simply involve incubating the amplification reaction mixture containing the DNase for a short period of time, for example 1 to 10 minutes at room temperature, conveniently 2 to 5 minutes. The time of this incubation is not critical and may vary depending on the exact DNase and concentration used, and the other components of the reaction system. The temperature may be any temperature at which the enzyme is active i.e. below the inactivation temperature (e.g. 37° C.), but room temperature is convenient.

Such a reaction mixture may, as mentioned above, contain all the necessary reactants for the amplification reaction, aside from the template i.e. the target nucleic acid to be amplified.

A typical representative PCR amplification reaction mixture may for example include:

| Component | Final Concentration |
| --- | --- |
| dATP | 50-200 µM |
| dCTP | 50-200 µM |
| dGTP | 50-200 µM |
| dTTP | 50-200 µM |
| Primer 1 | 0.05-0.2 µM |
| Primer 2 | 0.05-0.2 µM |
| DNA polymerase | 1-2.5 Units |
| ds DNase of SEQ ID NO:7 | 0.1-2 Units |
| MgCl$_2$ | 1.5-3.0 mM |
| PCR Buffer | 1X |
| Sterile distilled water | to final 50-100 µl |
| Experimental template (to be added after inactivation of DNase) | 50 pg-100 ng |
| Total Mix | 25-50 µl |

In the above representative example, any combination of sterile distilled water and 20 experimental template volumes can be used as long as the total volume of the reaction (including buffer, dNTPs, primers, enzymes and MgCl$_2$ solutions)

equals 25-50 μl. However, alternative final volumes may be used according to choice, to achieve e.g. similar or other desired final concentrations of reactants. Any convenient or commercially available PCR buffer may be used.

After decontamination, the DNase is inactivated by heating the reaction mixture. Conveniently this may be achieved by heating in the first PCR cycle.

Optimal performance of the PCR process is influenced by choice of temperature, time at temperature, and length of time between temperatures for each step in the cycle. A typical cycling profile for utilizing DNase to degrade contaminating ds DNA prior to PCR amplification of freshly added target nucleic acid is as follows: (a) 0 to 10 minutes of DNase incubation at room temperature; (b) 2 minutes of DNase inactivation at 94° C.; (c) addition of template; 1 minute of DNA melting at 94° C.; (d) 15 seconds of primer annealing at 50-65° C.; (e) 30 seconds of primer extending at 72° C.; (f) 10 seconds of DNA melting at 94° C.; and steps (d)-(f) are repeated as many times as necessary to obtain the desired level of amplification.

As mentioned previously the DNase of the invention is especially suited to a one step reverse transcription amplification reaction, for instance reverse transcription PCR. Such protocols are well established in the art but, for completeness, a typical representative reverse transcription PCR mixture may for example include:

| Component | Final Concentration |
|---|---|
| dATP | 50-200 μM |
| dCTP | 50-200 μM |
| dGTP | 50-200 μM |
| dTTP | 50-200 μM |
| Primer 1 | 0.05-0.2 μM |
| Primer 2 | 0.05-0.2 μM |
| AMV reverse transcriptase | 10-200 Units |
| DNA polymerase | 1-2.5 Units |
| ds DNase of SEQ ID NO:7 | 0.1-2 Units |
| MgCl$_2$ | 3.0-6.0 mM |
| PCR buffer | 1X |
| Sterile distilled water | to final 25-50 μl |
| Experimental RNA template | 50 pg-100 ng |
| Total Mix | 25-50 μl |

The above discussion in relation to volumes and buffers in reverse transcription and PCR reactions are applicable here. After decontamination, the reverse transcriptase reaction is performed at a temperature at which the DNase is inactivated (e.g. 50° C. for one 25 hour). During this step the DNase is inactivated. This means that the cDNA product will not be degraded as it is produced and when the PCR reaction begins there is no degradation of that product either. After the reverse transcription reaction the PCR reaction is performed without further addition to the reaction mixtures by exposing the reaction vessels to a cycling profile such as the profile described above.

The invention will now be described by way of non-limiting Examples with reference to the following figures in which:

FIG. 1 shows photographs of a number of agarose gels which show the activity of the DNase of SEQ ID NO:7 and the wild type *Pandalus borealis* DNase (SEQ ID NO:6) which have been inactivated in the presence or absence of DTT at 50, 55, 65 or 94° C. for 15, 30 or 60 minutes against plasmid DNA at 37° C. for 3 hours.

FIG. 4 shows the amino sequence of mature form P214A mutant *Pandalus borealis* DNase of the invention (SEQ ID NO:7).

FIG. 5 shows is the coding nucleotide sequence of the P214A mutant of the mature form of *Pandalus borealis* DNase (SEQ ID No. 8).

FIG. 6 shows the nucleotide sequence and amino acid sequence of the P237A mutant *Pandalus borealis* DNase of the invention (SEQ ID NO:3 and 4). This amino acid sequence includes the signal peptide MIGRTTFIALFVKVLTIWSFTKG (SEQ ID NO:9).

FIG. 7 shows the amino acid sequence of the mature form of the DNase of *Pandalus borealis* (SEQ ID NO:5).

FIG. 8 shows the coding nucleotide sequence of the mature form of *Pandalus borealis* DNase (SEQ ID No. 6).

FIG. 9 shows the cDNA nucleotide sequence and translated amino acid sequence of the *Pandalus borealis* DNase (SEQ ID NO:1 and 2). This amino acid sequence includes the signal peptide MIGRTTFIALFVKVLTIWSFTKG (SEQ ID NO:9).

FIG. 11 shows the amino acid sequence alignment of king crab (*Paralithodes camtschaticus*) DNase (SEQ ID No. 15) and *Pandalus borealis* DNase (SEQ ID No. 5). 65.7% identity in 379 residues overlap; Score: 1384.0; Gap frequency: 0.0%.

Figure 12:
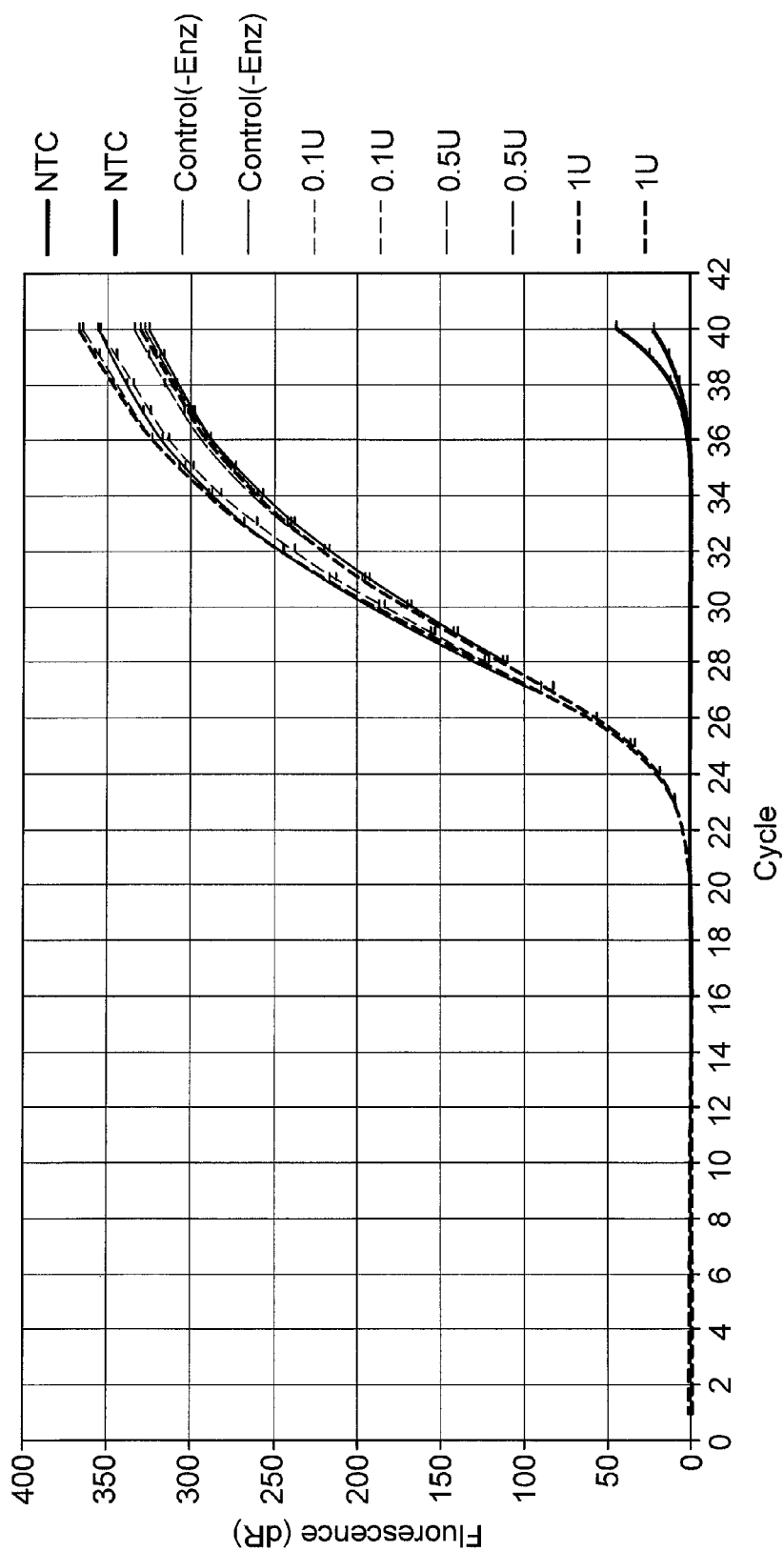

FIG. 12 shows the effect of increasing concentrations of P214A mutant on a quantitative PCR protocol.

Figure 13:
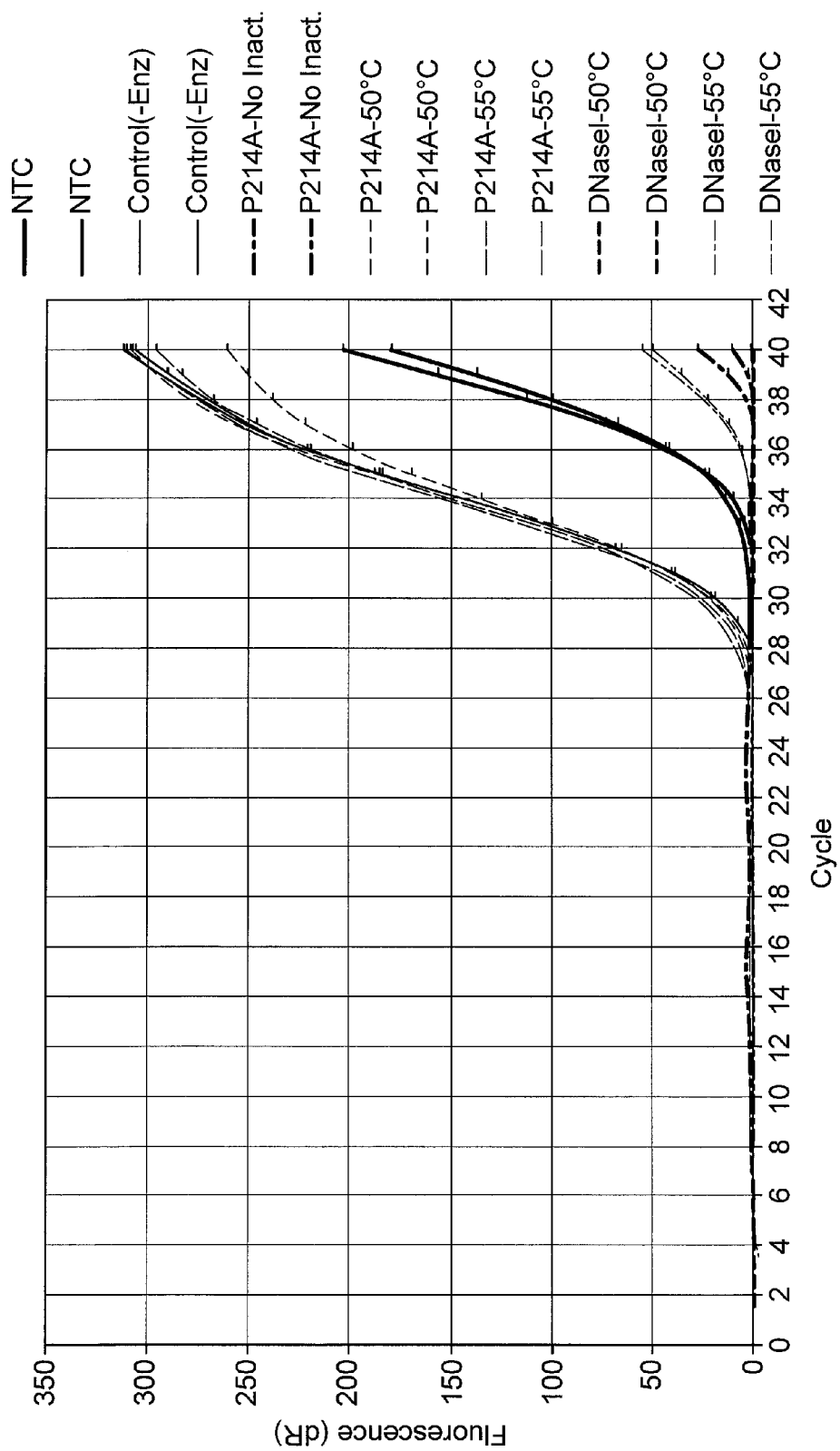

FIG. 13 shows a comparison of the thermolability of DNase I and P214A mutant through measuring the inhibitory effects of heat treated enzymes on a quantitative PCR protocol.

Figure 14:
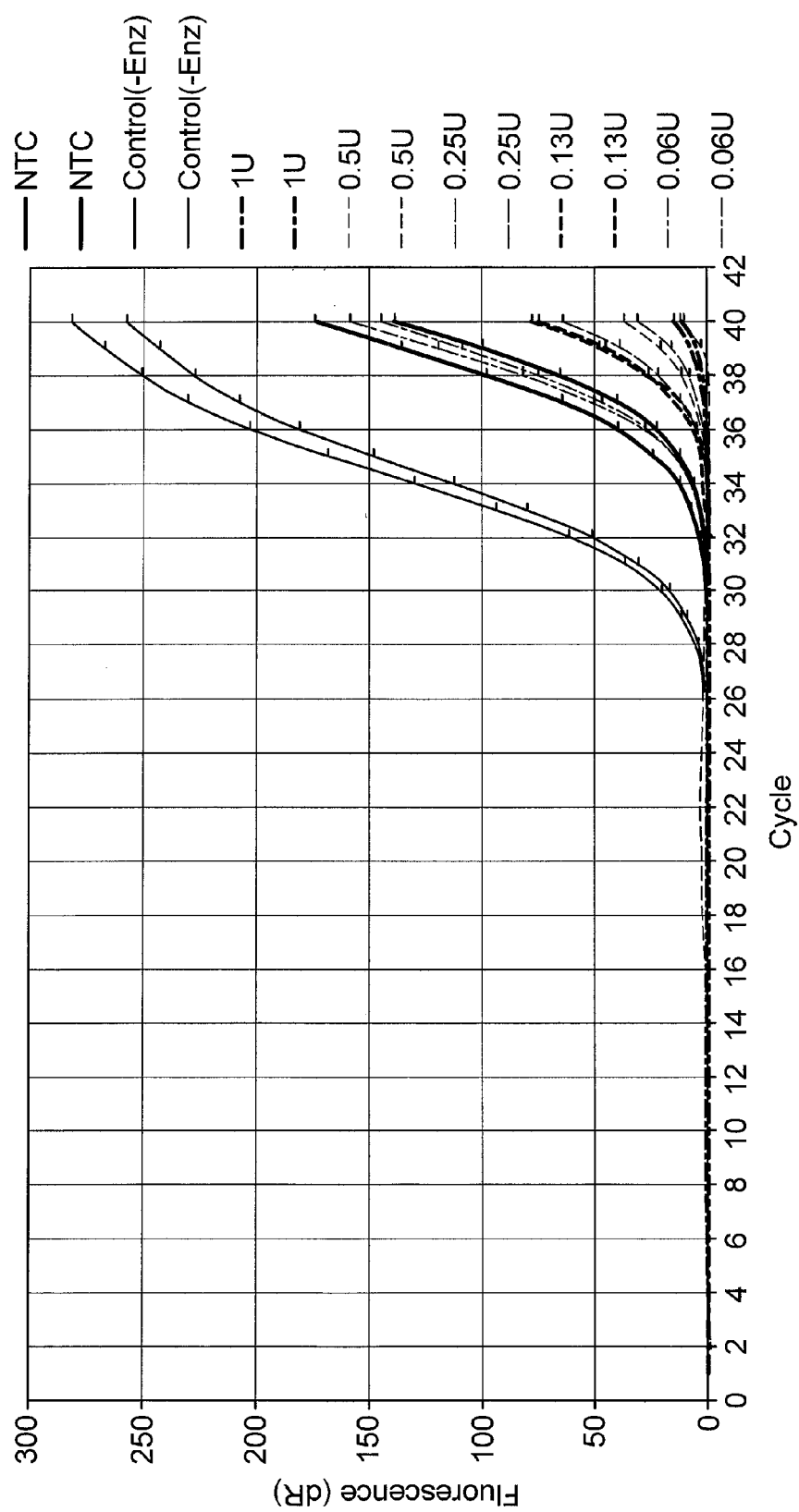

FIG. 14 shows the degree of removal of spiked DNA from a quantitative PCR reaction mix with increasing amounts of P214A mutant.

Figure 15:
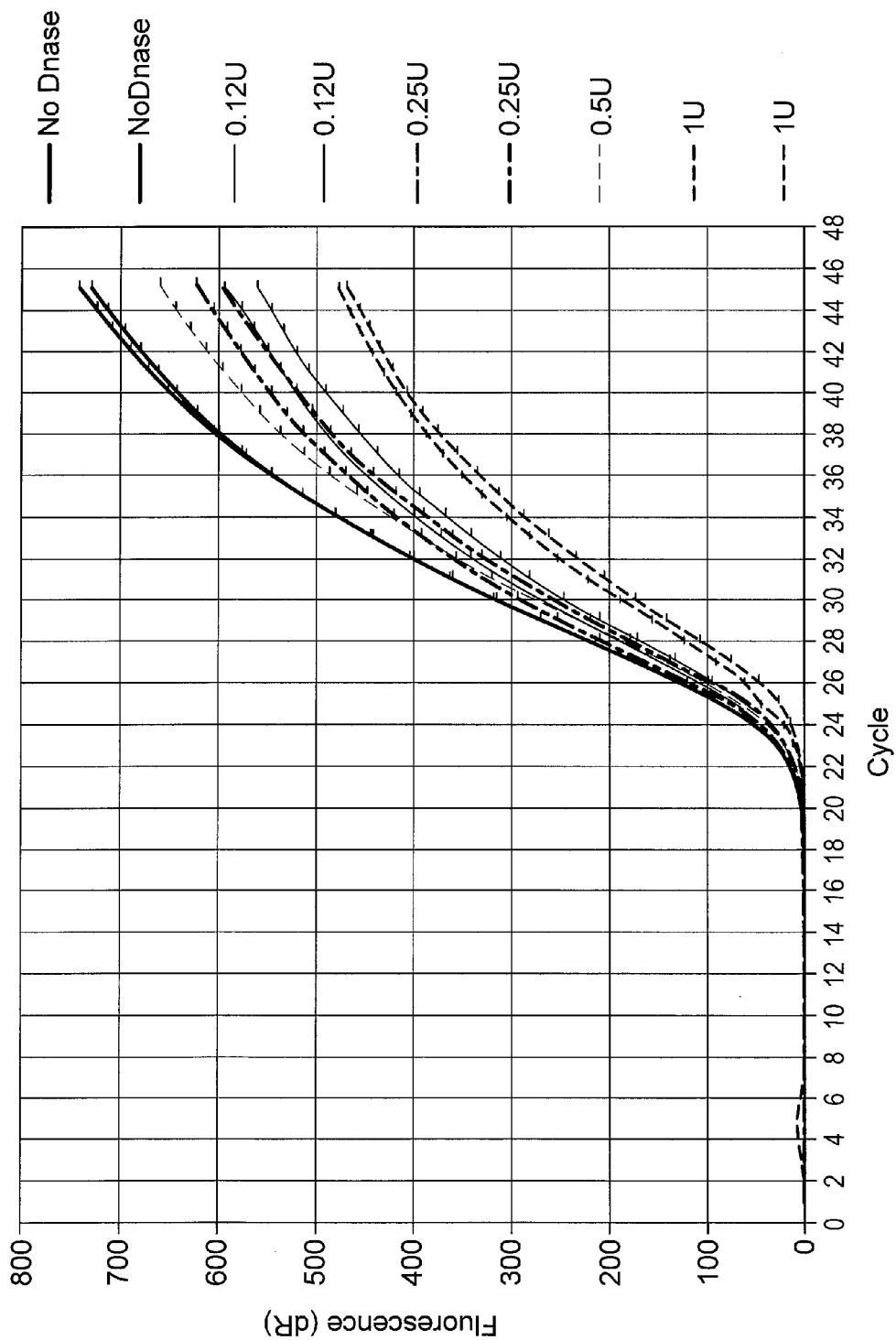

FIG. 15 shows the effect of increasing concentrations of P214A mutant on a one step RT-PCR reaction.

Figure 16:
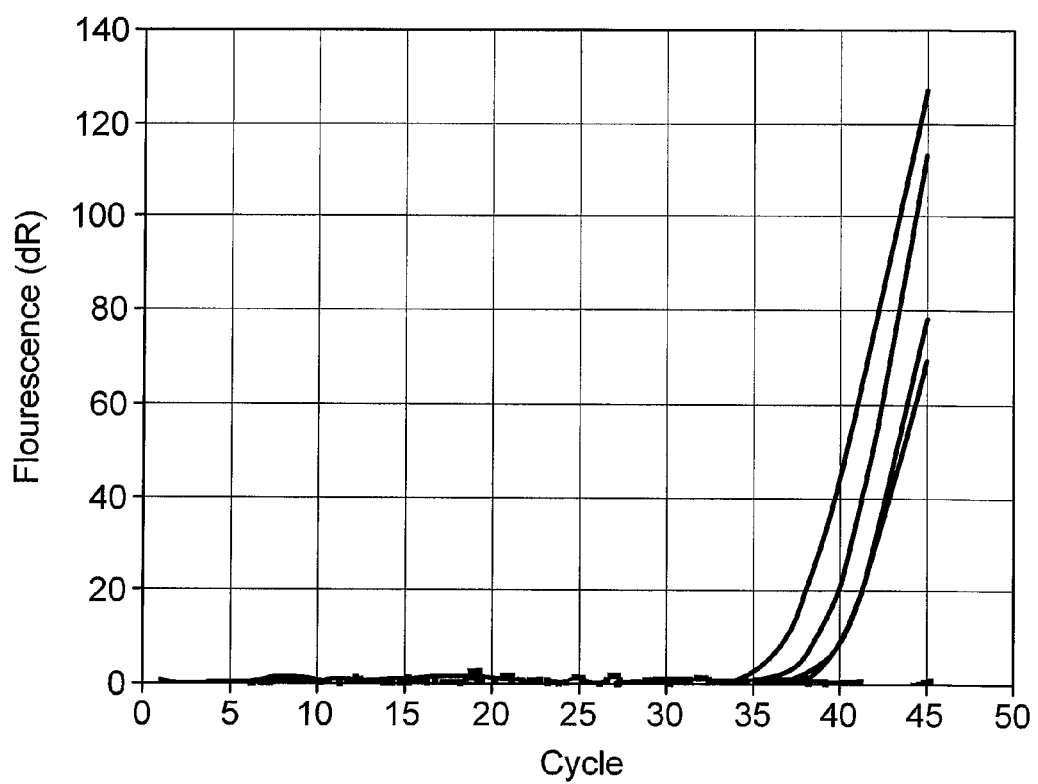

FIG. 16 shows the effect of P214A mutant on no template qPCR controls.

and in which

SEQ ID No. 1 is the amino acid sequence of the translated portion of the cDNA nucleotide sequence of the *Pandalus borealis* DNase.

SEQ ID No. 2 is the cDNA nucleotide sequence of the *Pandalus borealis* DNase.

SEQ ID No. 3 is the amino acid sequence of the P237A mutant *Pandalus borealis* DNase.

SEQ ID No. 4 is the coding nucleotide sequence of P237A mutant *Pandalus borealis* DNase.

SEQ ID No. 5 is the amino acid sequence of mature form of *Pandalus borealis* DNase.

SEQ ID No. 6 is the coding nucleotide sequence of the mature form of *Pandalus borealis* DNase.

SEQ ID No. 7 is the amino acid sequence of the P214A mutant of the mature form of *Pandalus borealis* DNase.

SEQ ID No. 8 is the coding nucleotide sequence of the P214A mutant of the mature form of *Pandalus borealis* DNase.

SEQ ID No. 9 is the amino acid sequence of the signal peptide of *Pandalus borealis* DNase.

SEQ ID No. 10 is an 5' FAM and 3' TAMRA labelled oligonucleotide for measuring DNase activity.

SEQ ID No. 11 is the complementary sequence of SEQ ID No. 10.

SEQ ID No. 12 is a forward primer for amplifying a section of the *E. coli* 23SrRNA gene.

SEQ ID No. 13 is a reverse primer for amplifying a section of the *E. coli* 23SrRNA gene.
SEQ ID No. 14 is a 5' FAM and 3' BHQ labelled oligonucleotide probe complementary to a section of the *E. coli* 23SrRNA gene between the regions complementary to SEQ ID No. 13 and SEQ ID No. 14.
SEQ ID No. 15 is the amino acid sequence of the King Crab (*Paralithodes camtschaticus*) DNase.
Sequence Listing Free Text
SEQ ID No. 10
<223> 5' FAM and 3' TAMRA labelled oligonucleotide probe for measuring DNase activity.
SEQ ID No. 11
<223> complementary sequence of SEQ ID No. 10.
SEQ ID No. 12
<223> forward primer for amplifying a section of the *E. coli* 23SrRNA gene.
SEQ ID No. 13
<223> reverse primer for amplifying a section of the *E. coli* 23SrRNA gene.
SEQ ID No. 14
<223> 5' FAM and 3' BHQ labelled oligonucleotide probe complementary to a section of the *E. coli* 23SrRNA gene between the regions complementary to SEQ ID No. 13 and SEQ ID No. 14.

EXAMPLE 1

Measurement of DNase Activity

Kunitz Assay

DNase activity may be assayed according to the procedure of Kunitz (Kunitz, M., 1950, Crystalline Deoxyribonuclease, II, Digestion of Thymus Nucleic Acid. The Kinetics of Reaction. J. Gen. Physiol., 33, 363-377). Ten μl of enzyme preparation is added to 50 pg calf thymus DNA in 100 mM sodium acetate, pH 5.0, 5 mM $MgCl_2$, in a final volume of 1 ml. The mixture is incubated at 25° C. and increase in absorption is measured at 260 nm. 1 U=0.001 $OD_{260}$ increase×$min^{-1}$.

The Modified Kunitz Assay of Yamamoto

The modified Kunitz assay, an endpoint assay, described by Yamamoto (Yamamoto, M. 1971. Purification and some properties of an acid deoxyribonuclease from testes of Chinook salmon *Oncorhynchus tshawytscha*. Biochim Biophys Acta, 228, 95-104) is a more sensitive version of the Kunitz assay and is considered to be more suitable for the measurement of residual DNase activity following inactivation. Ten μl enzyme is added 25 to 200 pg calf thymus DNA in 20 mM Tris/HCl, pH 8.0, 5 mM $MgCl_2$, in a final volume of 1 ml. The mixture is incubated at 37° C. for 20 minutes. Then 0.5 ml ice-cold 12% $HClO_4$ is added, thoroughly mixed, and left on ice for 20 minutes. The tubes are centrifuged on full speed in an Eppendorf centrifuge for 10 minutes. Absorption at 260 nm is determined from which the Units are calculated. 1 U=0.001 $OD_{260}$ increase×$min^{-1}$.

EXAMPLE 2

Mutation of *Pandalus borealis* DNase

*Pandalus borealis* DNase (SEQ ID No. 5) was mutated at residue 214 (corresponding to residue 237 in SEQ ID No 1) using the Quick-Change™ mutagenesis kit from Invitrogen and the manufacturers instructions. Proline is the wild type residue and alanine was the replacement residue. FIGS. 4 to 9 show the amino acid and nucleotide sequences of the wild type and the mutated versions of the *Pandalus borealis* DNase. Mutants were sequenced and found to be correct and transformed in *Pichia pastoris*. A transformant was obtained that showed a good expression, similar to the wild type. Initial inactivation tests on the P214A mutant showed it to be more easily inactivated at 55° C. than the wild type DNase.

The recombinant *Pichia pastoris* clone containing the mutant P214A DNase expression cassette was then expressed in a one-liter fermentor. The fermentation was done as described in *Pichia* fermentation process guidelines, Invitrogen. The fermentate (approximate 1 l) was centrifuged 4500 g for 15 minutes to remove the cells, and the supernatant was poured into a new bottle. pH was then adjusted to 8 by adding 0.5 M NaOH and then it was centrifuged for 4500 g for 15 minutes to remove precipitated salts. The new supernatant was finally filtered through a Whatman GF/F filter.

P214A DNase protein was initially purified using anion exchange chromatography. The pH adjusted and filtered supernatant (1150 ml) was applied to a Q-Sepharose FF column (2.6/10) equilibrated with 25 mM Tris/HCl pH 8, 5 mM $MgCl_2$, 0.25 M NaCl (Buffer A). The column was then washed with 19 column volumes buffer A and then the P214A protein was eluted with buffer 25 mM Tris/HCl pH 8, 5 mM MgCl2, 0.5 M NaCl. Fractions of 10 ml were collected. The flow rate used was 10 ml/min. Fractions containing the P214A protein were selected by measuring activity according to the Kunitz method described in Example 1.

The selected fractions were pooled and dialyzed in 10 mM Tris/HCl, pH 7.5, 5 mM $MgCl_2$ (Buffer B) at 4° C. The volume of the dialyzed sample was adjusted to 200 ml using the same buffer and was then applied to a Blue Sepharose FF column (5.0/10) equilibrated with buffer B. The column was washed with 2 column volumes of buffer B and the P214A DNase protein was eluted using buffer B+0.25 M NaCl, and fractions of 10 ml were collected. The flow rate used was 10 ml/min. Finally, the P214A containing fractions were selected by measuring the activity as described above, pooled, and concentrated.

EXAMPLE 3

Determination of Residual Activity after Inactivation at Different Temperatures

To determine if the P214A mutant is completely inactivated by heat, the integrity of a PCR-product in presence of heat-inactivated P214A mutant or the wild type enzyme was assessed.

Enzyme (0.8 U P214A, or 1.5 U wt) was added to PCR tubes containing a total volume of 20 μl in a 25 mM Tris/HCl, pH 8, 5 mM $MgCl_2$, ±1 mM DTT buffer. The enzymes were heat inactivated for 15, 30 and 60 minutes at various temperatures and the tubes were thereafter placed on ice. 0.5 pg of a purified ~500 by PCR product was added and reactions were incubated for 3 hours at 37° C. Finally the reactions were analyzed using agarose gel electrophoresis. A negative control (no enzyme) and a positive control (100× diluted enzyme added after the heat-inactivation step) were treated in the same way as the reactions above.

FIG. 1 summarizes the heat-inactivation experiments of the P214A mutant compared to the wild type enzyme at 50° C., 55° C., 65° C. and 94° C. The no-enzyme control (−) show the intact PCR-product, whereas the positive control (+), 100 times diluted enzyme not heat-inactivated, illustrates the effect of 1% residual activity.

From control experiments, no visible degradation of the PCR product indicates less than 0.01% residual activity (results not shown), which is the detection limit when using ~1

U enzyme in the assay. At 50° C. and 55° C. only the P214A mutant is completely heat-inactivated, demonstrating the effect of the P214A substitution. Addition of DTT (1 mM in this experiment) is necessary for complete inactivation of both enzymes. Only when incubated for 60 min at 94° C. a complete heat-inactivation seen in the absence of DTT.

EXAMPLE 4

Timecourse of Inactivation of P214A at 50° C. and 55° C.

If a DNase is used to decontaminate a complete reverse transcriptase reaction mixture it is important that it is inactivated early in the reverse transcriptase step. If the nuclease is not immediately inactivated it could start to cleave the cDNA and have a detrimental effect on the reverse transcription products. This is especially important if the reverse transcription is part of a quantitative assay to measure the amount of RNA in a sample. Inactivation of the P214A mutant DNase at 50° C. and 55° C. at shorter time points was therefore tested.

P214A, 12.5-125 U, was diluted in a typical RT-buffer (50 mM Tris/HCl, pH 8.3, 50 mM KCl, 5 mM $MgCl_2$, 5 mM DTT) in a total volume of 25 µl. Samples were incubated at 50 and 55° C. in a PCR machine for 0-5 minutes. Then remaining activity was measured using the modified Kunitz assay as described in Example 1.

Figure 2:
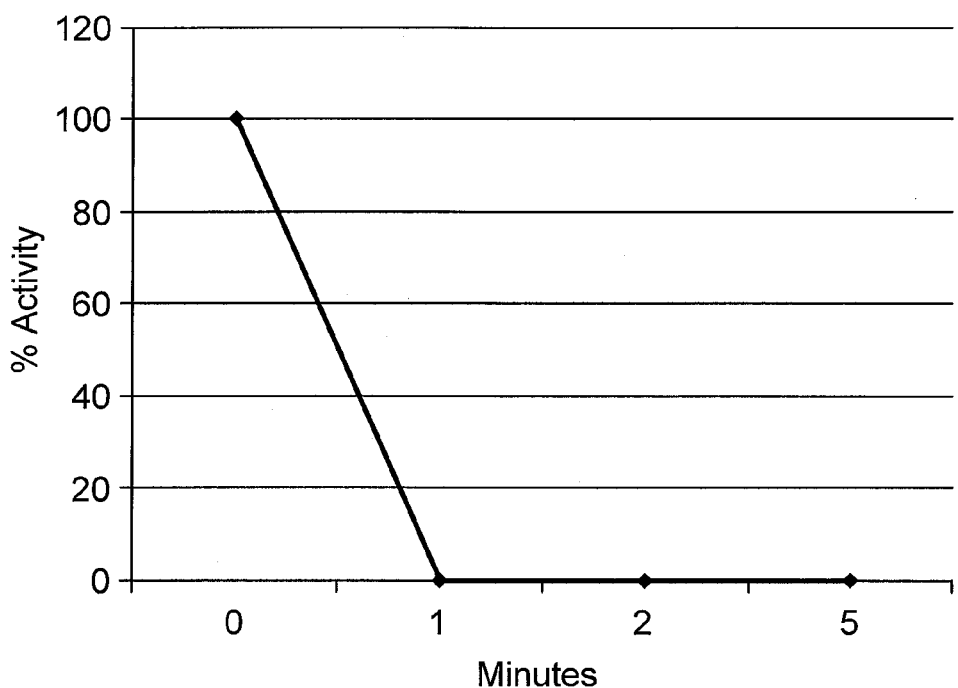
FIG. 2 shows the timecourse of inactivation of the DNase of SEQ ID NO:7 at 55° C. in the presence of DTT.
Figure 3:
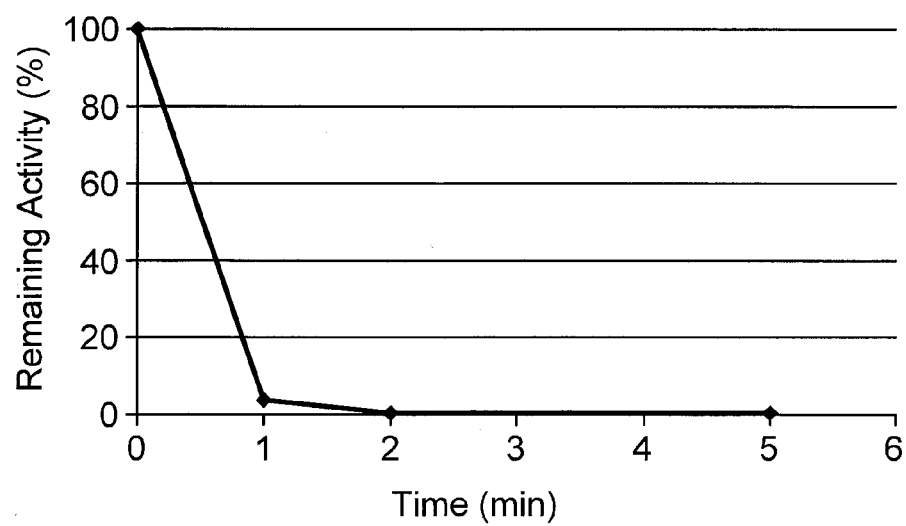
FIG. 3 shows the timecourse of inactivation of the DNase of SEQ ID NO:7 at 50° C. in the presence of DTT.

As can be seen from FIGS. 2 and 3, the P214A mutant can be completely inactivated within 1 minute at 55° C. and almost completely inactivated within one minute at 50° C.

EXAMPLE 5

Effect of wild type and *Pandalus borealis* DNase and P214A Mutant on Efficiency of One-Step RT-PCR One step qRT-PCR amplification reactions were performed using the Brilliant QRT-PCR Master Mix Kit 1-Step (Stratagene), and thermocycling and detection in a Smart Cycler II (Cepheid).

The reaction mix (25 µl) contained 12.5 µl 2×QRT-PCR master mix, 1.25 µl 20× primer/probe mix (GAPDH HS99999905_m1, Applied Biosystems), 0.1 µl Stratascript reverse transcriptase, 1 µl DNase enzyme. As a template, 1 µl (1 ng/µl) of Stratagene QPCR Human Reference Total RNA (Stratagene) was used. Each reaction mixture was pre-incubated 30° C. for 15 minutes. Then one-step reverse transcription PCR was done at 50° C. for 30 min, 95° C. for 10 min, followed by 45 cycles of 94° C. for 15 sec, 60° C. for 1 min.

Figure 10:
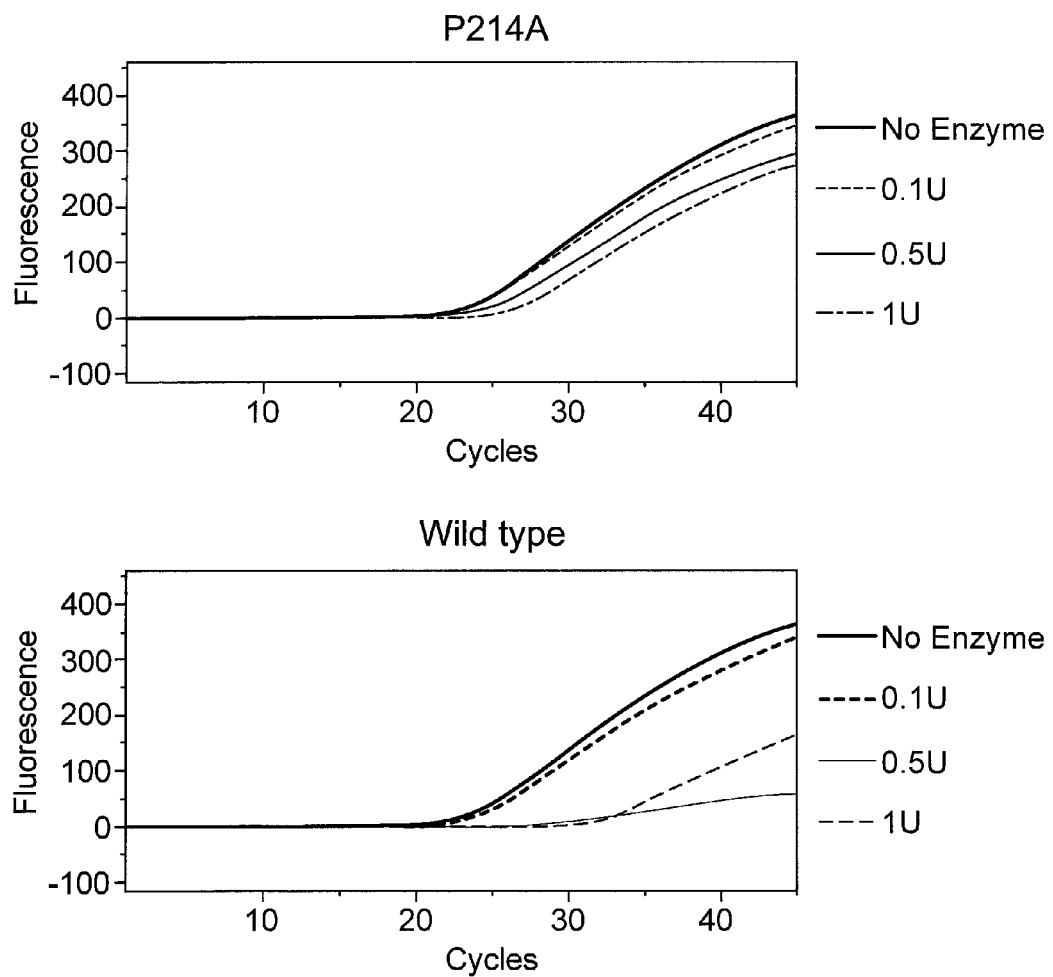
FIG. 10 shows the effect of wild type *Pandalus borealis* DNase and P214A mutant on efficiency of one-step RT-PCR.

As shown in FIG. 10, little or no effect on RT-PCR efficiency is observed in samples containing the P214A mutant. On the other hand, the wild type nuclease severely affects the efficiency of the RT-PCR.

EXAMPLE 6

Analysis of ds/ssDNA Specificities for P214A

The specificity for double- and single stranded DNA for P214A was tested by measuring fluorescence from oligonucleotides labelled with the fluorophore FAM (fluorescein) at the 5' terminus and with TAMRA at the 3'terminus. Cleavage of the oligonucleotide by the nuclease would result in an increase of fluorescence from FAM that was measured in a fluorimeter with excitation wavelength 485 nm and emission wavelength 520 nm. A double stranded DNA substrate was prepared by mixing the labelled oligonucleotide with a second oligonucleotide that was complementary to the labelled oligonucleotide.

37 Units of the P214A mutant was added to a reaction mixture that contained 50 mM Tris/HCl, pH 8.0, 5 mM $MgCl_2$ and 0.2 µM labelled oligonucleotide (DNAsub) (total volume 100 µL). The mixture was incubated at 25° C. in a white welled microtiterplate for fluoroscopy.

Similarly, 0.2 µM complementary oligonucleotide, compDNAsub, was added to a reaction mixture as above to form a double stranded DNA substrate. 0.01 Unit P214A mutant was then added to the reaction mixture.

Fluorescence over time was measured in a Victor3 instrument and the activity was calculated as the initial increase of fluorescence per minute, corrected for the increase of fluorescence without nuclease (blank reaction), and expressed as (fluorescence units/minute)/Kunitz Unit.

For double stranded DNA substrate, the result was 211,922 (fluorescence units/min)/Kunitz Unit, and for single stranded DNA substrate the result was 10.4 (fluorescence units/min)/Kunitz Unit. Accordingly, the double stranded DNA substrate is degraded at a rate 20,366 faster than single stranded DNA. Oligonucleotides:

```
DNAsub:
5'-FAM-CGCCATCGGAGGTTC-TAMRA-3'    [SEQ ID NO: 10]

compDNAsub:
5'-GAACCTCCGATGGCG-3'              [SEQ ID NO: 11]
```

EXAMPLE 7 qPCR Decontamination Using the P214A Mutant

Materials and Methods

*Escherichia coli* TOP10 genomic DNA was isolated using DNeasy Blood and Tissue Kit (Qiagen), and DNA concentration was measured using Quant-iT dsDNA BR assay kit and Qubit fluorimeter (Life Technologies). For detection and quantification of *E. coli* genomic DNA using quantitative PCR (qPCR), a small region of the highly conserved 23S rRNA gene was used to design a primer/probe set as described in (Smith G J III et. al.; 1999; Biotechniques 26(3):518-22, 524, 526). This gene is present in seven copies in the *E. coli* genome.

In general, qPCR was done in a Smart Cycler II (Cepheid) in 25 µl reactions containing 12.5 µl 2× Brilliant qPCR master mix (Stratagene) or TaqMan Gene Expression master mix (Applied Biosystems), 3 µM of each primer and 1 µM probe, 1 mM DTT, 1 or 10 pg *E. coli* genomic DNA, and various amounts of P214A mutant enzyme or DNaseI (Sigma). qPCR reaction was performed as follows: 95° C. for 10 minutes, followed by 40 cycles of 95° C. for 15 seconds and 60° C. for 1 minute.

Primers/Probe:

```
Ecoli_23S_fwd:
                                   [SEQ ID No. 12]
5'-GAAAGGCGCGCGATACAG-3'

Ecoli_23S_rev:
                                   [SEQ ID No. 13]
5'-GTCCCGCCCTACTCATCG A-3'
```

```
            -continued
Ecoli_23S_probe:
                                         [SEQ ID No. 14]
   5'-FAM-CCCCGTACACAAAAATGCACATGCTG-BHQ-3'
```

Effect of P214A Mutant on Primer/Probe Integrity (ssDNA)

This experiment tested whether the P214A mutant has an inhibitory affect on a qPCR protocol through degradation of the primers/probe in a qPCR mix (i.e. degradation of single stranded DNA).

Reaction mixes as described above (Brilliant qPCR master mix) were set up without template (E. coli genomic) DNA and incubated at 37° C. for 10 minutes. An inactivation step of 95° C. for 10 minutes was done before adding 10 pg of E. coli genomic DNA as a template. qPCR amplification was then performed as described above.

The 37° C. incubation step allows the P214A mutant to catalyse that degradation of DNA. The 95° C. incubation for 10 minutes completely inactivates the mutant before the template DNA is added. Any inhibition of the qPCR results can therefore only be due to a nuclease activity against ssDNA (the primers/probe have been degraded). As shown in FIG. 12, the qPCR result is not affected by adding up to 1 U of P214A mutant, indicating that it has no measurable activity against the primers/probe in the qPCR reaction mix.

Comparison of Thermolability of DNaseI and P214A Mutant in a qPCR Protocol

Reaction mixes as described above were set up without template DNA in the presence or absence of DNaseI (1 U) or P214A (1 U). An incubation step of 37° C. for 10 minutes was then followed by an inactivation step of 50° C. or 55° C. for 15 minutes. 1 pg of E. coli genomic DNA was then added to the mixtures and qPCR was performed as described above.

To account for variable reaction setup-times in qPCR experiments, the reaction mixes were incubated at room-temperature for 15 min before being subjected to amplification. Any residual DNase activity in the reaction mix will degrade the template DNA and will inhibit the qPCR results.

As illustrated in FIG. 13, the P214A mutant does not inhibit the qPCR compared to the control reaction (Control (-Enz); no enzyme added), and so can be considered to be completely inactivated by a 15 min 50° C. incubation step in this experiment. The DNaseI enzyme is not inactivated, and Ct is shifted by more than 8, indicating high remaining activity after the inactivation step or/and activity against the primers/probe in the reaction mix.

Removal of Spiked DNA from qPCR Reaction Mixtures

To test the ability of the P214A mutant to remove "contaminating" DNA, various amounts of P214A mutant to the qPCR reaction mixes described above (TaqMan Gene Expression master mix) spiked with 1 pg of E. coli genomic DNA. The reaction mixtures were then incubated for 10 minutes at 37° C. and then incubated at 60° C. for 15 minutes. The results are shown in FIG. 14. As can be seen, 0.25 U or more of the P214A mutant per 25 µl reaction mixture causes the Ct to increase by more than 8. This indicates a >250 fold reduction in the concentration of the spiked DNA.

In addition to the individual results discussed above, it should be noted that the no template controls (NTC) gave positive results for both the Brilliant qPCR master mix (Stratagene), and the TaqMan Gene Expression Master mix (Applied Biosystems). This illustrates the problem of contaminating DNA in qPCR mixes when using universal primers targeting bacterial or E. coli DNA for detecting or diagnosing bacteria.

EXAMPLE 8

Effect of P214A Mutant on Efficiency of One-Step RT-PCR

The experiment described in Example 5 was repeated with several concentrations of the P214A mutant to investigate how increasing amounts of the enzyme affected the sensitivity of the RT-PCR reaction. Five different concentrations ranging from 0 to 1 U of DNase were tested and the results are displayed in FIG. 15. Using 0.1-0.5 U of DNase does not affect the sensitivity of the RT-PCR. Using 1 U of the enzyme decreases the sensitivity with a Ct of 1.5.

EXAMPLE 9

Removal of Bacterial DNA Contaminants from Commercial PCR Products

It has been shown (Example 7) that traces of bacterial DNA are often present in commercial nucleic acid amplification reaction mixtures (so called "master mixes"). In qPCR experiments for detecting pathogens this is often a problem as amplification of these contaminants leads to false positives, including in the No Template Controls (NTCs). In this example, 1 U of P214A mutant DNase was added to qPCR master mixes from four different suppliers and preincubated for 10 minutes at 37° C. Following this, the master mixes were incubated at 60° C. for 15 minutes, and compared to non-treated master mixes in a qPCR reaction as described in Example 7. No template was added to any reaction. The results are shown in FIG. 16 and it can be seen that only the master mixes preincubated with the enzyme give negative NTCs.

The invention claimed is:

1. A DNase or an enzymatically active fragment thereof, said DNase having the sequence of SEQ ID No. 1 or a sequence which is at least 90% identical thereto, but wherein the proline residue at position 237 of SEQ ID No 1, or the equivalent proline in other sequences, has been modified or substituted, said DNase or enzymatically active fragment thereof being substantially irreversibly inactivated by heating at a temperature of about 50° C. for 5 mins in a buffer consisting of 25 mM Tris HCI, pH 8.5,5 mM MgCl$_2$ and 1 mM DTT, and being substantially specific for double stranded DNA.

2. A DNase or an enzymatically active fragment thereof as claimed in claim 1, wherein said DNase has the sequence of SEQ ID No. 5 or a sequence which is at least 90% identical thereto, but wherein the proline residue at position 214 of SEQ ID No 5, or the equivalent proline in other sequences, has been modified or substituted, said DNase or enzymatically active fragment thereof being substantially irreversibly inactivated by heating at a temperature of about 50° C. for 5 mins in a buffer consisting of 25 mM Tris HCI, pH 8.5, 5 mM MgCl$_2$ and 1 mM DTT, and being substantially specific for double stranded DNA.

3. A DNase or a fragment thereof as claimed in claim 1, said DNase having the sequence of a DNase obtainable from a species from the phylum Arthropodoa, but wherein the proline residue equivalent to the proline at position 237 of SEQ ID No 1 has been modified deleted or substituted.

4. A DNase or a fragment thereof as claimed in claim 3, said DNase having the sequence of a DNase obtainable from a species from a subphylum selected from Crustacea, Hexpoda, Chelicerata or Myriapoda, but wherein the proline residue equivalent to the proline at position 237 of SEQ ID No 1 has been modified or substituted.

5. A DNase or a fragment thereof as claimed in claim 3, said DNase having the sequence of a DNase obtainable from a species selected from *Pandalus borealis, Paralithodes camtschaticus* (king crab), *Marspenus japonicus* (kuruma shrimp) or *Penaeus japonicus*, but wherein the proline residue equivalent to the proline at position 237 of SEQ ID No 1 has been modified or substituted.

6. A DNase or a fragment thereof as claimed in claim 5 said DNase having the sequence of a DNase obtainable from *Pandalus borealis* but wherein the proline residue equivalent to the proline at position 237 of SEQ ID No 1 has been modified or substituted.

7. A DNase as claimed in claim 1, said DNase having the sequence of SEQ ID NO:3 or SEQ ID NO:7.

8. A kit or composition comprising a DNase as claimed in claim 1 and optionally one or more of the following
   (i) a nucleotide triphosphate;
   (ii) an oligonucleotide primer;
   (iii) a reverse transcription enzyme;
   (iv) a DNA polymerases;
   (v) a DNA ligase; and
   (vi) a restriction enzyme.

9. A DNase or fragment thereof as claimed in claim 1 wherein said DNase has a sequence which is at least 95% identical to SEQ ID No. 1, but wherein the proline residue equivalent to position 237 of SEQ ID No. 1 has been modified, deleted or substituted.

10. A DNase or fragment thereof as claimed in claim 1 wherein said DNase has a sequence which is at least 98% identical to SEQ ID No. 1, but wherein the proline residue equivalent to position 237 of SEQ ID No. 1 has been modified, deleted or substituted.

11. A DNase or fragment thereof as claimed in claim 2 wherein said DNase has a sequence which is at least 95% identical to SEQ ID No. 5, but wherein the proline residue equivalent to position 214 of SEQ ID No. 5 has been modified, deleted or substituted.

12. A DNase or fragment thereof as claimed in claim 2 wherein said DNase has a sequence which is at least 98% identical to SEQ ID No. 5, but wherein the proline residue equivalent to position 214 of SEQ ID No. 5 has been modified, deleted or substituted.

13. A method of removing nucleic acid contamination from a reverse transcription reaction which comprises the use of the DNase or enzymatically active fragment thereof of claim 1.

14. A method of removing nucleic acid contamination from a hot-start PCR, wherein said reaction is a barrier hot-start PCR set up and/or involves a hot-start DNA polymerase, which method comprises the use of the DNase or enzymatically active fragment thereof of claim 1.

15. A method as claimed in claim 13 or 14, wherein a reverse transcription reaction mixture, a hot-start PCR set up, a hot-start PCR mixture, or any of the individual components thereof is contacted with the DNase under conditions which permit digestion of any contaminating double stranded DNA and thereafter the reaction mixture is heated to inactivate the DNase or enzymatically active fragment thereof.

16. A method of in vitro reverse transcription of a target nucleic acid, wherein said method includes a step of treating the reverse transcription reaction mixture with the DNase or enzymatically active fragment thereof of claim 1, prior to commencement of the actual reverse transcription reaction.

17. A method as claimed in claim 15, wherein the reverse transcription reaction mixture is a complete mixture and is heated at the working temperature of the reverse transcription enzyme to inactivate the DNase or enzymatically active fragment thereof.

18. A method of as claimed in claim 13 or 16, wherein said reverse transcription reaction is followed by a nucleic acid amplification reaction.

19. A method as claimed in claim 18, wherein said nucleic acid amplification reaction is PCR, LCR, SDA, 3SR or LAMP, preferably PCR.

20. A method as claimed in claim 18, wherein the reverse transcription reaction and the amplification reaction are performed in a single reaction vessel.

21. A method of hot-start PCR, wherein said reaction is a barrier hot-start PCR set up and/or involves a hot-start DNA polymerase, wherein said method includes a step of treating the hot-start PCR set up/mixture or the hot-start DNA polymerase with the DNase or enzymatically active fragment thereof of claim 1, prior to commencement of the hot start PCR.

22. A method as claimed in claim 16, wherein the reverse transcription reaction mixture is a complete mixture and is heated at the working temperature of the reverse transcription enzyme to inactivate the DNase.

\* \* \* \* \*

UNITED STATES PATENT AND TRADEMARK OFFICE
CERTIFICATE OF CORRECTION

PATENT NO. : 8,551,753 B2
APPLICATION NO. : 12/840552
DATED : October 8, 2013
INVENTOR(S) : Lanes et al.

Page 1 of 1

It is certified that error appears in the above-identified patent and that said Letters Patent is hereby corrected as shown below:

On the title page, below Item (22) add the following:

--(30)       Foreign Application Priority Data

21 July 2009 (GB) ......................................0912637.6--

Signed and Sealed this
Twelfth Day of November, 2013

Teresa Stanek Rea
*Deputy Director of the United States Patent and Trademark Office*

SEQUENCE LISTING

```
<160> NUMBER OF SEQ ID NOS: 15

<210> SEQ ID NO 1
<211> LENGTH: 404
<212> TYPE: PRT
<213> ORGANISM: Pandalus borealis
<220> FEATURE:
<221> NAME/KEY: SIGNAL
<222> LOCATION: (1)..(23)
```

<400> SEQUENCE: 1

```
Met Ile Gly Arg Thr Thr Phe Ile Ala Leu Phe Val Lys Val Leu Thr
1               5                   10                  15

Ile Trp Ser Phe Thr Lys Gly Glu Asp Cys Val Trp Asp Asn Asp Val
            20                  25                  30

Asp Tyr Pro Glu Tyr Pro Leu Ile Leu Asp Ser Ser Phe Gln Leu
        35                  40                  45

Val Leu Pro Val Leu Glu Gly Asp Gln Arg Ile Thr Ser Val Gln Ser
50                  55                  60

Gly Ser Lys Leu Ile Leu Ala Cys Pro Gly Arg Gly Ile Ser Ala Leu
65                  70                  75                  80

Gly Ser Glu Asp Ala Gln Ala Thr Cys Leu Gly Gly Lys Leu Val Glu
                85                  90                  95

Val Asp Gly Lys Glu Trp Asn Ile Val Glu Leu Gly Cys Thr Lys Met
            100                 105                 110

Ala Ser Glu Thr Ile His Arg Asn Leu Gly Gln Cys Gly Asp Gln Asp
        115                 120                 125

Leu Gly Ile Tyr Glu Val Ile Gly Phe Asp Leu Pro Thr Thr Gly His
130                 135                 140

Phe Tyr Glu Leu Ile Arg Val Cys Phe Asp Pro Ala Asn Glu Thr Thr
145                 150                 155                 160

Ile Phe Ser Glu Asn Ile Val His Gly Ala Ser Ile Ala Ala Lys Asp
            165                 170                 175

Ile Asp Pro Gly Arg Pro Ser Phe Lys Thr Ser Thr Gly Phe Phe Ser
        180                 185                 190

Val Ser Met Ile Ser Val Tyr Ser Gln Arg Ser Gln Leu Glu Leu Met
195                 200                 205

Lys Asn Leu Leu Gly Asp Asp Glu Leu Ala Ala Thr Ile Ile Asp Pro
210                 215                 220

Ser Glu Gln Phe Tyr Phe Ala Lys Gly His Met Ala Pro Asp Ala Asp
225                 230                 235                 240

Phe Val Thr Val Val Glu Gln Asp Ala Thr Tyr Tyr Tyr Ile Asn Ala
            245                 250                 255

Leu Pro Gln Trp Gln Ala Phe Asn Asn Gly Asn Trp Lys Tyr Leu Glu
        260                 265                 270

Tyr Asp Thr Arg Asp Leu Ala Glu Lys His Gly Thr Asp Leu Thr Val
        275                 280                 285

Tyr Ser Gly Gly Trp Gly Val Leu Glu Leu Glu Asp Ile Asn Gly Asn
290                 295                 300

Pro Val Glu Ile Tyr Leu Gly Leu Ala Gln Asp Lys Lys Val Val Pro
305                 310                 315                 320

Ala Pro Ala Leu Thr Trp Lys Val Ile Tyr Glu Lys Asp Thr Asn Arg
            325                 330                 335

Ala Ala Ala Ile Val Gly Ile Asn Asn Pro His Ile Thr Thr Ala Pro
            340                 345                 350

Glu Pro Leu Cys Thr Asp Ile Cys Ser Ser Leu Thr Trp Leu Asp Phe
        355                 360                 365

Asp Phe Gly Asp Leu Val His Gly Tyr Thr Tyr Cys Cys Ser Val Ala
        370                 375                 380

Asp Leu Arg Ala Ala Ile Pro Asn Val Pro Leu Gly Asp Val Asp
385                 390                 395                 400

Ile Leu Asp Glu
```

-continued

```
<210> SEQ ID NO 2
<211> LENGTH: 1791
<212> TYPE: DNA
<213> ORGANISM: Pandalus borealis
<220> FEATURE:
<221> NAME/KEY: CDS
<222> LOCATION: (23)..(1237)
<220> FEATURE:
<221> NAME/KEY: sig_peptide
<222> LOCATION: (23)..(91)

<400> SEQUENCE: 2
```

| | | | | | | | | | | | | |
|---|---|---|---|---|---|---|---|---|---|---|---|---|
| cagtcagaac tgttgaggag ca | atg<br>Met<br>1 | ata<br>Ile | ggc<br>Gly | cgg<br>Arg | acc<br>Thr<br>5 | act<br>Thr | ttc<br>Phe | ata<br>Ile | gct<br>Ala | tta<br>Leu<br>10 | | 52 |
| ttc<br>Phe | gta<br>Val | aaa<br>Lys | gtt<br>Val | ctg<br>Leu<br>15 | act<br>Thr | att<br>Ile | tgg<br>Trp | agc<br>Ser | ttt<br>Phe<br>20 | acc<br>Thr | aaa<br>Lys | ggt<br>Gly | gag<br>Glu | gac<br>Asp<br>25 | tgt<br>Cys | 100 |
| gtc<br>Val | tgg<br>Trp | gac<br>Asp | aat<br>Asn<br>30 | gat<br>Asp | gta<br>Val | gac<br>Asp | tat<br>Tyr | cct<br>Pro<br>35 | gag<br>Glu | tat<br>Tyr | cct<br>Pro | cct<br>Pro | ctg<br>Leu<br>40 | atc<br>Ile | ctg<br>Leu | 148 |
| gat<br>Asp | tca<br>Ser | tcc<br>Ser<br>45 | ttt<br>Phe | cag<br>Gln | ctg<br>Leu | gtt<br>Val | ctg<br>Leu<br>50 | cca<br>Pro | gtg<br>Val | ttg<br>Leu | gaa<br>Glu | gga<br>Gly<br>55 | gac<br>Asp | caa<br>Gln | agg<br>Arg | 196 |
| ata<br>Ile | acc<br>Thr<br>60 | agt<br>Ser | gtc<br>Val | caa<br>Gln | tct<br>Ser | ggg<br>Gly<br>65 | agt<br>Ser | aag<br>Lys | ctg<br>Leu | atc<br>Ile | ttg<br>Leu<br>70 | gct<br>Ala | tgt<br>Cys | cct<br>Pro | ggg<br>Gly | 244 |
| agg<br>Arg<br>75 | gga<br>Gly | att<br>Ile | tca<br>Ser | gcc<br>Ala | ctg<br>Leu<br>80 | ggg<br>Gly | tca<br>Ser | gag<br>Glu | gat<br>Asp | gca<br>Ala<br>85 | caa<br>Gln | gcc<br>Ala | act<br>Thr | tgt<br>Cys | ctt<br>Leu<br>90 | 292 |
| ggt<br>Gly | ggc<br>Gly | aag<br>Lys | ctc<br>Leu | gtc<br>Val<br>95 | gaa<br>Glu | gtc<br>Val | gat<br>Asp | ggc<br>Gly | aaa<br>Lys<br>100 | gaa<br>Glu | tgg<br>Trp | aat<br>Asn | ata<br>Ile | gtc<br>Val<br>105 | gaa<br>Glu | 340 |
| ctc<br>Leu | ggc<br>Gly | tgc<br>Cys | aca<br>Thr<br>110 | aaa<br>Lys | atg<br>Met | gca<br>Ala | tct<br>Ser | gaa<br>Glu<br>115 | acc<br>Thr | atc<br>Ile | cat<br>His | aga<br>Arg | aac<br>Asn<br>120 | ctt<br>Leu | gga<br>Gly | 388 |
| caa<br>Gln | tgt<br>Cys | ggt<br>Gly<br>125 | gat<br>Asp | caa<br>Gln | gac<br>Asp | ctg<br>Leu | gga<br>Gly<br>130 | att<br>Ile | tac<br>Tyr | gaa<br>Glu | gtc<br>Val | att<br>Ile<br>135 | ggt<br>Gly | ttc<br>Phe | gac<br>Asp | 436 |
| ctt<br>Leu | cca<br>Pro<br>140 | aca<br>Thr | acg<br>Thr | gga<br>Gly | cac<br>His | ttc<br>Phe<br>145 | tat<br>Tyr | gaa<br>Glu | ttg<br>Leu | ata<br>Ile | cga<br>Arg<br>150 | gtt<br>Val | tgc<br>Cys | ttt<br>Phe | gac<br>Asp | 484 |
| ccg<br>Pro<br>155 | gca<br>Ala | aat<br>Asn | gag<br>Glu | acc<br>Thr | act<br>Thr<br>160 | att<br>Ile | ttt<br>Phe | tcc<br>Ser | gag<br>Glu | aac<br>Asn<br>165 | atc<br>Ile | gtt<br>Val | cac<br>His | gga<br>Gly | gcc<br>Ala<br>170 | 532 |
| agc<br>Ser | atc<br>Ile | gcc<br>Ala | gcc<br>Ala | aaa<br>Lys<br>175 | gac<br>Asp | att<br>Ile | gac<br>Asp | ccg<br>Pro | ggt<br>Gly<br>180 | cgt<br>Arg | cca<br>Pro | tct<br>Ser | ttc<br>Phe | aaa<br>Lys<br>185 | aca<br>Thr | 580 |
| tcc<br>Ser | act<br>Thr | ggg<br>Gly<br>190 | ttc<br>Phe | ttc<br>Phe | agt<br>Ser | gta<br>Val | tcg<br>Ser<br>195 | atg<br>Met | ata<br>Ile | tct<br>Ser | gtc<br>Val | tat<br>Tyr<br>200 | tcg<br>Ser | caa<br>Gln | aga<br>Arg | 628 |
| agt<br>Ser | cag<br>Gln<br>205 | ctg<br>Leu | gag<br>Glu | ctc<br>Leu | atg<br>Met | aag<br>Lys<br>210 | aac<br>Asn | ctc<br>Leu | tta<br>Leu | gga<br>Gly | gat<br>Asp<br>215 | gat<br>Asp | gaa<br>Glu | tta<br>Leu | gct<br>Ala | 676 |
| gcg<br>Ala | aca<br>Thr<br>220 | atc<br>Ile | atc<br>Ile | gat<br>Asp | cct<br>Pro | tca<br>Ser<br>225 | gag<br>Glu | cag<br>Gln | ttc<br>Phe | tac<br>Tyr | ttt<br>Phe<br>230 | gct<br>Ala | aaa<br>Lys | gga<br>Gly | cat<br>His | 724 |
| atg<br>Met<br>235 | gct<br>Ala | cct<br>Pro | gac<br>Asp | gcg<br>Ala | gac<br>Asp<br>240 | ttt<br>Phe | gtg<br>Val | aca<br>Thr | gta<br>Val | gtt<br>Val<br>245 | gag<br>Glu | cag<br>Gln | gac<br>Asp | gca<br>Ala | aca<br>Thr<br>250 | 772 |
| tac<br>Tyr | tat<br>Tyr | tac<br>Tyr | atc<br>Ile | aac<br>Asn | gcg<br>Ala | ttg<br>Leu | cct<br>Pro | caa<br>Gln | tgg<br>Trp | cag<br>Gln | gcc<br>Ala | ttt<br>Phe | aac<br>Asn | aat<br>Asn | gga<br>Gly | 820 |

```
                        255                 260                 265
aac tgg aag tac ttg gaa tac gac acc cgt gac ctg gct gaa aaa cat        868
Asn Trp Lys Tyr Leu Glu Tyr Asp Thr Arg Asp Leu Ala Glu Lys His
                270                 275                 280 ggc act gac ctg acc gtc tac agt ggt ggc tgg ggg gtt cta gag ctt        916
Gly Thr Asp Leu Thr Val Tyr Ser Gly Gly Trp Gly Val Leu Glu Leu
            285                 290                 295 gaa gac atc aac gga aac ccc gtt gaa atc tat ctt ggc ctc gcc cag        964
Glu Asp Ile Asn Gly Asn Pro Val Glu Ile Tyr Leu Gly Leu Ala Gln
        300                 305                 310 gac aaa aaa gtt gtc cct gct cct gca tta aca tgg aag gtg atc tat       1012
Asp Lys Lys Val Val Pro Ala Pro Ala Leu Thr Trp Lys Val Ile Tyr
315                 320                 325                 330 gag aag gac act aac cga gct gct gct att gtt gga ata aac aac ccc       1060
Glu Lys Asp Thr Asn Arg Ala Ala Ala Ile Val Gly Ile Asn Asn Pro
                335                 340                 345 cac atc acc acg gca cca gaa cct ctt tgt acc gac atc tgc tcc agc       1108
His Ile Thr Thr Ala Pro Glu Pro Leu Cys Thr Asp Ile Cys Ser Ser
            350                 355                 360 ctc aca tgg ctg gac ttt gat ttt ggg gac ctt gtc cat ggc tac acc       1156
Leu Thr Trp Leu Asp Phe Asp Phe Gly Asp Leu Val His Gly Tyr Thr
        365                 370                 375 tac tgc tgc tct gta gct gat ctc agg gca gcc att ccc aat gtt cca       1204
Tyr Cys Cys Ser Val Ala Asp Leu Arg Ala Ala Ile Pro Asn Val Pro
380                 385                 390 gat tta gga gac gtt gat atc tta gac gaa taa agatattca cgtactacaa      1257
Asp Leu Gly Asp Val Asp Ile Leu Asp Glu
395                 400 ccatacaaag agagtgattg ctgtacccttt aactaaaggt ctggacctgg taacatgctt    1317
atgtagttaa tggtgtcgag gaattcatca atcagagrag aactacttca aagagggaaa    1377
aattaatcgc aatttttgtt cattacaagt ataatactta tcttattaca atttcgagta    1437 cgatttttaaa ggatakatcc acacacttat gcacaaagtg atcatcaagt tatacagtct   1497
tcattaaaac ataagcagtc attacggcat gtttcattca gaagttttca agatattgat   1557
tgccattctc gatttcttga aagatgtgca cacatgtgga gaagaaatgt aaacatctta   1617
aaattcatac tctggatatc cagatattat gcacacaaaa tgtcaagtct cctgcctgct   1677
tctttggaaa gatgtgcata tgcacgcaca tgtaaccatg agattcacaa aatgtaatca   1737
tctcttaatc aaaacctaat cagtcattca aaaaaaaaaa aaaaaaaaaa aaaa          1791

<210> SEQ ID NO 3
<211> LENGTH: 404
<212> TYPE: PRT
<213> ORGANISM: Pandalus borealis
<220> FEATURE:
<221> NAME/KEY: SIGNAL
<222> LOCATION: (1)..(23)
<220> FEATURE:
<221> NAME/KEY: MUTAGEN
<222> LOCATION: (237)..(237)

<400> SEQUENCE: 3

Met Ile Gly Arg Thr Thr Phe Ile Ala Leu Phe Val Lys Val Leu Thr
1               5                   10                  15

Ile Trp Ser Phe Thr Lys Gly Glu Asp Cys Val Trp Asp Asn Asp Val
            20                  25                  30

Asp Tyr Pro Glu Tyr Pro Pro Leu Ile Leu Asp Ser Ser Phe Gln Leu
        35                  40                  45

Val Leu Pro Val Leu Glu Gly Asp Gln Arg Ile Thr Ser Val Gln Ser
```

```
                50                  55                  60
Gly Ser Lys Leu Ile Leu Ala Cys Pro Gly Arg Gly Ile Ser Ala Leu
 65                  70                  75                  80

Gly Ser Glu Asp Ala Gln Ala Thr Cys Leu Gly Gly Lys Leu Val Glu
                 85                  90                  95

Val Asp Gly Lys Glu Trp Asn Ile Val Glu Leu Gly Cys Thr Lys Met
                100                 105                 110

Ala Ser Glu Thr Ile His Arg Asn Leu Gly Gln Cys Gly Asp Gln Asp
                115                 120                 125

Leu Gly Ile Tyr Glu Val Ile Gly Phe Asp Leu Pro Thr Thr Gly His
            130                 135                 140

Phe Tyr Glu Leu Ile Arg Val Cys Phe Asp Pro Ala Asn Glu Thr Thr
145                 150                 155                 160

Ile Phe Ser Glu Asn Ile Val His Gly Ala Ser Ile Ala Ala Lys Asp
                165                 170                 175

Ile Asp Pro Gly Arg Pro Ser Phe Lys Thr Ser Thr Gly Phe Phe Ser
                180                 185                 190

Val Ser Met Ile Ser Val Tyr Ser Gln Arg Ser Gln Leu Glu Leu Met
            195                 200                 205

Lys Asn Leu Leu Gly Asp Asp Glu Leu Ala Ala Thr Ile Ile Asp Pro
210                 215                 220

Ser Glu Gln Phe Tyr Phe Ala Lys Gly His Met Ala Ala Asp Ala Asp
225                 230                 235                 240

Phe Val Thr Val Val Glu Gln Asp Ala Thr Tyr Tyr Tyr Ile Asn Ala
                245                 250                 255

Leu Pro Gln Trp Gln Ala Phe Asn Asn Gly Asn Trp Lys Tyr Leu Glu
                260                 265                 270

Tyr Asp Thr Arg Asp Leu Ala Glu Lys His Gly Thr Asp Leu Thr Val
            275                 280                 285

Tyr Ser Gly Gly Trp Gly Val Leu Glu Leu Glu Asp Ile Asn Gly Asn
        290                 295                 300

Pro Val Glu Ile Tyr Leu Gly Leu Ala Gln Asp Lys Lys Val Val Pro
305                 310                 315                 320

Ala Pro Ala Leu Thr Trp Lys Val Ile Tyr Glu Lys Asp Thr Asn Arg
                325                 330                 335

Ala Ala Ala Ile Val Gly Ile Asn Asn Pro His Ile Thr Thr Ala Pro
                340                 345                 350

Glu Pro Leu Cys Thr Asp Ile Cys Ser Ser Leu Thr Trp Leu Asp Phe
            355                 360                 365

Asp Phe Gly Asp Leu Val His Gly Tyr Thr Tyr Cys Cys Ser Val Ala
        370                 375                 380

Asp Leu Arg Ala Ala Ile Pro Asn Val Pro Asp Leu Gly Asp Val Asp
385                 390                 395                 400

Ile Leu Asp Glu

<210> SEQ ID NO 4
<211> LENGTH: 1791
<212> TYPE: DNA
<213> ORGANISM: Pandalus borealis
<220> FEATURE:
<221> NAME/KEY: CDS
<222> LOCATION: (23)..(1237)
<220> FEATURE:
<221> NAME/KEY: sig_peptide
<222> LOCATION: (23)..(91)
<220> FEATURE:
<221> NAME/KEY: mutation
```

-continued

<222> LOCATION: (731)..(731)

<400> SEQUENCE: 4

```
cagtcagaac tgttgaggag ca atg ata ggc cgg acc act ttc ata gct tta         52
                        Met Ile Gly Arg Thr Thr Phe Ile Ala Leu
                         1               5                  10 ttc gta aaa gtt ctg act att tgg agc ttt acc aaa ggt gag gac tgt         100
Phe Val Lys Val Leu Thr Ile Trp Ser Phe Thr Lys Gly Glu Asp Cys
            15                  20                  25 gtc tgg gac aat gat gta gac tat cct gag tat cct cct ctg atc ctg         148
Val Trp Asp Asn Asp Val Asp Tyr Pro Glu Tyr Pro Pro Leu Ile Leu
        30                  35                  40 gat tca tcc ttt cag ctg gtt ctg cca gtg ttg gaa gga gac caa agg         196
Asp Ser Ser Phe Gln Leu Val Leu Pro Val Leu Glu Gly Asp Gln Arg
    45                  50                  55 ata acc agt gtc caa tct ggg agt aag ctg atc ttg gct tgt cct ggg         244
Ile Thr Ser Val Gln Ser Gly Ser Lys Leu Ile Leu Ala Cys Pro Gly
60                  65                  70 agg gga att tca gcc ctg ggg tca gag gat gca caa gcc act tgt ctt         292
Arg Gly Ile Ser Ala Leu Gly Ser Glu Asp Ala Gln Ala Thr Cys Leu
 75                  80                  85                  90 ggt ggc aag ctc gtc gaa gtc gat ggc aaa gaa tgg aat ata gtc gaa         340
Gly Gly Lys Leu Val Glu Val Asp Gly Lys Glu Trp Asn Ile Val Glu
                 95                 100                 105 ctc ggc tgc aca aaa atg gca tct gaa acc atc cat aga aac ctt gga         388
Leu Gly Cys Thr Lys Met Ala Ser Glu Thr Ile His Arg Asn Leu Gly
            110                 115                 120 caa tgt ggt gat caa gac ctg gga att tac gaa gtc att ggt ttc gac         436
Gln Cys Gly Asp Gln Asp Leu Gly Ile Tyr Glu Val Ile Gly Phe Asp
        125                 130                 135 ctt cca aca acg gga cac ttc tat gaa ttg ata cga gtt tgc ttt gac         484
Leu Pro Thr Thr Gly His Phe Tyr Glu Leu Ile Arg Val Cys Phe Asp
    140                 145                 150 ccg gca aat gag acc act att ttt tcc gag aac atc gtt cac gga gcc         532
Pro Ala Asn Glu Thr Thr Ile Phe Ser Glu Asn Ile Val His Gly Ala
155                 160                 165                 170 agc atc gcc gcc aaa gac att gac ccg ggt cgt cca tct ttc aaa aca         580
Ser Ile Ala Ala Lys Asp Ile Asp Pro Gly Arg Pro Ser Phe Lys Thr
                175                 180                 185 tcc act ggg ttc ttc agt gta tcg atg ata tct gtc tat tcg caa aga         628
Ser Thr Gly Phe Phe Ser Val Ser Met Ile Ser Val Tyr Ser Gln Arg
            190                 195                 200 agt cag ctg gag ctc atg aag aac ctc tta gga gat gat gaa tta gct         676
Ser Gln Leu Glu Leu Met Lys Asn Leu Leu Gly Asp Asp Glu Leu Ala
        205                 210                 215 gcg aca atc atc gat cct tca gag cag ttc tac ttt gct aaa gga cat         724
Ala Thr Ile Ile Asp Pro Ser Glu Gln Phe Tyr Phe Ala Lys Gly His
    220                 225                 230 atg gct gct gac gcg gac ttt gtg aca gta gtt gag cag gac gca aca         772
Met Ala Ala Asp Ala Asp Phe Val Thr Val Val Glu Gln Asp Ala Thr
235                 240                 245                 250 tac tat tac atc aac gcg ttg cct caa tgg cag gcc ttt aac aat gga         820
Tyr Tyr Tyr Ile Asn Ala Leu Pro Gln Trp Gln Ala Phe Asn Asn Gly
                255                 260                 265 aac tgg aag tac ttg gaa tac gac acc cgt gac ctg gct gaa aaa cat         868
Asn Trp Lys Tyr Leu Glu Tyr Asp Thr Arg Asp Leu Ala Glu Lys His
            270                 275                 280 ggc act gac ctg acc gtc tac agt ggt ggc tgg ggg gtt cta gag ctt         916
Gly Thr Asp Leu Thr Val Tyr Ser Gly Gly Trp Gly Val Leu Glu Leu
        285                 290                 295
```

```
gaa gac atc aac gga aac ccc gtt gaa atc tat ctt ggc ctc gcc cag    964
Glu Asp Ile Asn Gly Asn Pro Val Glu Ile Tyr Leu Gly Leu Ala Gln
    300                 305                 310 gac aaa aaa gtt gtc cct gct cct gca tta aca tgg aag gtg atc tat   1012
Asp Lys Lys Val Val Pro Ala Pro Ala Leu Thr Trp Lys Val Ile Tyr
315                 320                 325                 330 gag aag gac act aac cga gct gct gct att gtt gga ata aac aac ccc   1060
Glu Lys Asp Thr Asn Arg Ala Ala Ala Ile Val Gly Ile Asn Asn Pro
                335                 340                 345 cac atc acc acg gca cca gaa cct ctt tgt acc gac atc tgc tcc agc   1108
His Ile Thr Thr Ala Pro Glu Pro Leu Cys Thr Asp Ile Cys Ser Ser
            350                 355                 360 ctc aca tgg ctg gac ttt gat ttt ggg gac ctt gtc cat ggc tac acc   1156
Leu Thr Trp Leu Asp Phe Asp Phe Gly Asp Leu Val His Gly Tyr Thr
        365                 370                 375 tac tgc tgc tct gta gct gat ctc agg gca gcc att ccc aat gtt cca   1204
Tyr Cys Cys Ser Val Ala Asp Leu Arg Ala Ala Ile Pro Asn Val Pro
    380                 385                 390 gat tta gga gac gtt gat atc tta gac gaa taa aagatattca cgtactacaa  1257
Asp Leu Gly Asp Val Asp Ile Leu Asp Glu
395                 400 ccatacaaag agagtgattg ctgtaccttt aactaaaggt ctggacctgg taacatgctt  1317
atgtagttaa tggtgtcgag gaattcatca atcagagrag aactacttca agagggaaa   1377 aattaatcgc aattttttgtt cattacaagt ataatactta tcttattaca atttcgagta 1437 cgatttttaaa ggatakatcc acacacttat gcacaaagtg atcatcaagt tatacagtct  1497
tcattaaaac ataagcagtc attacggcat gtttcattca aagttttca agatattgat  1557 tgccattctc gatttcttga agatgtgca cacatgtgga gaagaaaatgt aaacatctta  1617 aaattcatac tctggatatc cagatattat gcacacaaaa tgtcaagtct cctgcctgct  1677
tctttggaaa gatgtgcata tgcacgcaca tgtaaccatg agattcacaa aatgtaatca  1737
tctcttaatc aaaacctaat cagtcattca aaaaaaaaaa aaaaaaaaaa aaaa        1791

<210> SEQ ID NO 5
<211> LENGTH: 381
<212> TYPE: PRT
<213> ORGANISM: Pandalus borealis

<400> SEQUENCE: 5

Glu Asp Cys Val Trp Asp Asn Asp Val Asp Tyr Pro Glu Tyr Pro Pro
1               5                   10                  15

Leu Ile Leu Asp Ser Ser Phe Gln Leu Val Leu Pro Val Leu Glu Gly
            20                  25                  30

Asp Gln Arg Ile Thr Ser Val Gln Ser Gly Ser Lys Leu Ile Leu Ala
        35                  40                  45

Cys Pro Gly Arg Gly Ile Ser Ala Leu Gly Ser Glu Asp Ala Gln Ala
    50                  55                  60

Thr Cys Leu Gly Gly Lys Leu Val Glu Val Asp Gly Lys Glu Trp Asn
65                  70                  75                  80

Ile Val Glu Leu Gly Cys Thr Lys Met Ala Ser Glu Thr Ile His Arg
                85                  90                  95

Asn Leu Gly Gln Cys Gly Asp Gln Asp Leu Gly Ile Tyr Glu Val Ile
            100                 105                 110

Gly Phe Asp Leu Pro Thr Thr Gly His Phe Tyr Glu Leu Ile Arg Val
        115                 120                 125

Cys Phe Asp Pro Ala Asn Glu Thr Thr Ile Phe Ser Glu Asn Ile Val
    130                 135                 140
```

```
His Gly Ala Ser Ile Ala Ala Lys Asp Ile Asp Pro Gly Arg Pro Ser
145                 150                 155                 160

Phe Lys Thr Ser Thr Gly Phe Phe Ser Val Ser Met Ile Ser Val Tyr
            165                 170                 175

Ser Gln Arg Ser Gln Leu Glu Leu Met Lys Asn Leu Leu Gly Asp Asp
        180                 185                 190

Glu Leu Ala Ala Thr Ile Ile Asp Pro Ser Glu Gln Phe Tyr Phe Ala
    195                 200                 205

Lys Gly His Met Ala Pro Asp Ala Asp Phe Val Thr Val Val Glu Gln
210                 215                 220

Asp Ala Thr Tyr Tyr Tyr Ile Asn Ala Leu Pro Gln Trp Gln Ala Phe
225                 230                 235                 240

Asn Asn Gly Asn Trp Lys Tyr Leu Glu Tyr Asp Thr Arg Asp Leu Ala
            245                 250                 255

Glu Lys His Gly Thr Asp Leu Thr Val Tyr Ser Gly Gly Trp Gly Val
        260                 265                 270

Leu Glu Leu Glu Asp Ile Asn Gly Asn Pro Val Glu Ile Tyr Leu Gly
    275                 280                 285

Leu Ala Gln Asp Lys Lys Val Val Pro Ala Pro Ala Leu Thr Trp Lys
290                 295                 300

Val Ile Tyr Glu Lys Asp Thr Asn Arg Ala Ala Ala Ile Val Gly Ile
305                 310                 315                 320

Asn Asn Pro His Ile Thr Thr Ala Pro Glu Pro Leu Cys Thr Asp Ile
            325                 330                 335

Cys Ser Ser Leu Thr Trp Leu Asp Phe Asp Phe Gly Asp Leu Val His
        340                 345                 350

Gly Tyr Thr Tyr Cys Cys Ser Val Ala Asp Leu Arg Ala Ala Ile Pro
    355                 360                 365

Asn Val Pro Asp Leu Gly Asp Val Asp Ile Leu Asp Glu
370                 375                 380

<210> SEQ ID NO 6
<211> LENGTH: 1146
<212> TYPE: DNA
<213> ORGANISM: Pandalus borealis
<220> FEATURE:
<221> NAME/KEY: CDS
<222> LOCATION: (1)..(1146)

<400> SEQUENCE: 6 gag gac tgt gtc tgg gac aat gat gta gac tat cct gag tat cct cct      48
Glu Asp Cys Val Trp Asp Asn Asp Val Asp Tyr Pro Glu Tyr Pro Pro
1               5                   10                  15 ctg atc ctg gat tca tcc ttt cag ctg gtt ctg cca gtg ttg gaa gga      96
Leu Ile Leu Asp Ser Ser Phe Gln Leu Val Leu Pro Val Leu Glu Gly
            20                  25                  30 gac caa agg ata acc agt gtc caa tct ggg agt aag ctg atc ttg gct     144
Asp Gln Arg Ile Thr Ser Val Gln Ser Gly Ser Lys Leu Ile Leu Ala
        35                  40                  45 tgt cct ggg agg gga att tca gcc ctg ggt tca gag gat gca caa gcc     192
Cys Pro Gly Arg Gly Ile Ser Ala Leu Gly Ser Glu Asp Ala Gln Ala
50                  55                  60 act tgt ctt ggt ggc aag ctc gtc gaa gtc gat ggc aaa gaa tgg aat     240
Thr Cys Leu Gly Gly Lys Leu Val Glu Val Asp Gly Lys Glu Trp Asn
65                  70                  75                  80 ata gtc gaa ctc ggc tgc aca aaa atg gca tct gaa acc atc cat aga     288
Ile Val Glu Leu Gly Cys Thr Lys Met Ala Ser Glu Thr Ile His Arg
                85                  90                  95
```

```
aac ctt gga caa tgt ggt gat caa gac ctg gga att tac gaa gtc att        336
Asn Leu Gly Gln Cys Gly Asp Gln Asp Leu Gly Ile Tyr Glu Val Ile
            100                 105                 110 ggt ttc gac ctt cca aca acg gga cac ttc tat gaa ttg ata cga gtt        384
Gly Phe Asp Leu Pro Thr Thr Gly His Phe Tyr Glu Leu Ile Arg Val
        115                 120                 125 tgc ttt gac ccg gca aat gag acc act att ttt tcc gag aac atc gtt        432
Cys Phe Asp Pro Ala Asn Glu Thr Thr Ile Phe Ser Glu Asn Ile Val
130                 135                 140 cac gga gcc agc atc gcc gcc aaa gac att gac ccg ggt cgt cca tct        480
His Gly Ala Ser Ile Ala Ala Lys Asp Ile Asp Pro Gly Arg Pro Ser
145                 150                 155                 160 ttc aaa aca tcc act ggg ttc ttc agt gta tcg atg ata tct gtc tat        528
Phe Lys Thr Ser Thr Gly Phe Phe Ser Val Ser Met Ile Ser Val Tyr
                165                 170                 175 tcg caa aga agt cag ctg gag ctc atg aag aac ctc tta gga gat gat        576
Ser Gln Arg Ser Gln Leu Glu Leu Met Lys Asn Leu Leu Gly Asp Asp
            180                 185                 190 gaa tta gct gcg aca atc atc gat cct tca gag cag ttc tac ttt gct        624
Glu Leu Ala Ala Thr Ile Ile Asp Pro Ser Glu Gln Phe Tyr Phe Ala
        195                 200                 205 aaa gga cat atg gct cct gac gcg gac ttt gtg aca gta gtt gag cag        672
Lys Gly His Met Ala Pro Asp Ala Asp Phe Val Thr Val Val Glu Gln
210                 215                 220 gac gca aca tac tat tac atc aac gcg ttg cct caa tgg cag gcc ttt        720
Asp Ala Thr Tyr Tyr Tyr Ile Asn Ala Leu Pro Gln Trp Gln Ala Phe
225                 230                 235                 240 aac aat gga aac tgg aag tac ttg gaa tac gac acc cgt gac ctg gct        768
Asn Asn Gly Asn Trp Lys Tyr Leu Glu Tyr Asp Thr Arg Asp Leu Ala
                245                 250                 255 gaa aaa cat ggc act gac ctg acc gtc tac agt ggt ggc tgg ggg gtt        816
Glu Lys His Gly Thr Asp Leu Thr Val Tyr Ser Gly Gly Trp Gly Val
            260                 265                 270 cta gag ctt gaa gac atc aac gga aac ccc gtt gaa atc tat ctt ggc        864
Leu Glu Leu Glu Asp Ile Asn Gly Asn Pro Val Glu Ile Tyr Leu Gly
        275                 280                 285 ctc gcc cag gac aaa aaa gtt gtc cct gct cct gca tta aca tgg aag        912
Leu Ala Gln Asp Lys Lys Val Val Pro Ala Pro Ala Leu Thr Trp Lys
290                 295                 300 gtg atc tat gag aag gac act aac cga gct gct gct att gtt gga ata        960
Val Ile Tyr Glu Lys Asp Thr Asn Arg Ala Ala Ala Ile Val Gly Ile
305                 310                 315                 320 aac aac ccc cac atc acc acg gca cca gaa cct ctt tgt acc gac atc       1008
Asn Asn Pro His Ile Thr Thr Ala Pro Glu Pro Leu Cys Thr Asp Ile
                325                 330                 335 tgc tcc agc ctc aca tgg ctg gac ttt gat ttt ggg gac ctt gtc cat       1056
Cys Ser Ser Leu Thr Trp Leu Asp Phe Asp Phe Gly Asp Leu Val His
            340                 345                 350 ggc tac acc tac tgc tgc tct gta gct gat ctc agg gca gcc att ccc       1104
Gly Tyr Thr Tyr Cys Cys Ser Val Ala Asp Leu Arg Ala Ala Ile Pro
        355                 360                 365 aat gtt cca gat tta gga gac gtt gat atc tta gac gaa taa              1146
Asn Val Pro Asp Leu Gly Asp Val Asp Ile Leu Asp Glu
370                 375                 380

<210> SEQ ID NO 7
<211> LENGTH: 381
<212> TYPE: PRT
<213> ORGANISM: Pandalus borealis
<220> FEATURE:
<221> NAME/KEY: MUTAGEN
```

<222> LOCATION: (214)..(214)

<400> SEQUENCE: 7

| | | | | | | | | | | | | |
|---|---|---|---|---|---|---|---|---|---|---|---|---|
| Glu | Asp | Cys | Val | Trp | Asp | Asn | Asp | Val | Asp | Tyr | Pro | Glu | Tyr | Pro | Pro |
| 1 | | | | 5 | | | | | 10 | | | | | 15 | |

Glu Asp Cys Val Trp Asp Asn Asp Val Asp Tyr Pro Glu Tyr Pro Pro
1               5                   10                  15

Leu Ile Leu Asp Ser Ser Phe Gln Leu Val Leu Pro Val Leu Glu Gly
                20                  25                  30

Asp Gln Arg Ile Thr Ser Val Gln Ser Gly Ser Lys Leu Ile Leu Ala
            35                  40                  45

Cys Pro Gly Arg Gly Ile Ser Ala Leu Gly Ser Glu Asp Ala Gln Ala
        50                  55                  60

Thr Cys Leu Gly Gly Lys Leu Val Glu Val Asp Gly Lys Glu Trp Asn
65                  70                  75                  80

Ile Val Glu Leu Gly Cys Thr Lys Met Ala Ser Glu Thr Ile His Arg
                85                  90                  95

Asn Leu Gly Gln Cys Gly Asp Gln Asp Leu Gly Ile Tyr Glu Val Ile
            100                 105                 110

Gly Phe Asp Leu Pro Thr Thr Gly His Phe Tyr Glu Leu Ile Arg Val
        115                 120                 125

Cys Phe Asp Pro Ala Asn Glu Thr Thr Ile Phe Ser Glu Asn Ile Val
130                 135                 140

His Gly Ala Ser Ile Ala Ala Lys Asp Ile Asp Pro Gly Arg Pro Ser
145                 150                 155                 160

Phe Lys Thr Ser Thr Gly Phe Phe Ser Val Ser Met Ile Ser Val Tyr
                165                 170                 175

Ser Gln Arg Ser Gln Leu Glu Leu Met Lys Asn Leu Leu Gly Asp Asp
            180                 185                 190

Glu Leu Ala Ala Thr Ile Ile Asp Pro Ser Gln Phe Tyr Phe Ala
        195                 200                 205

Lys Gly His Met Ala Ala Asp Ala Asp Phe Val Thr Val Glu Gln
        210                 215                 220

Asp Ala Thr Tyr Tyr Ile Asn Ala Leu Pro Gln Trp Gln Ala Phe
225                 230                 235                 240

Asn Asn Gly Asn Trp Lys Tyr Leu Glu Tyr Asp Thr Arg Asp Leu Ala
                245                 250                 255

Glu Lys His Gly Thr Asp Leu Thr Val Tyr Ser Gly Trp Gly Val
            260                 265                 270

Leu Glu Leu Glu Asp Ile Asn Gly Asn Pro Val Glu Ile Tyr Leu Gly
        275                 280                 285

Leu Ala Gln Asp Lys Lys Val Val Pro Ala Pro Ala Leu Thr Trp Lys
290                 295                 300

Val Ile Tyr Glu Lys Asp Thr Asn Arg Ala Ala Ile Val Gly Ile
305                 310                 315                 320

Asn Asn Pro His Ile Thr Thr Ala Pro Glu Pro Leu Cys Thr Asp Ile
                325                 330                 335

Cys Ser Ser Leu Thr Trp Leu Asp Phe Asp Phe Gly Asp Leu Val His
            340                 345                 350

Gly Tyr Thr Tyr Cys Cys Ser Val Ala Asp Leu Arg Ala Ala Ile Pro
        355                 360                 365

Asn Val Pro Asp Leu Gly Asp Val Asp Ile Leu Asp Glu
370                 375                 380

<210> SEQ ID NO 8
<211> LENGTH: 1146
<212> TYPE: DNA

```
<213> ORGANISM: Pandalus borealis
<220> FEATURE:
<221> NAME/KEY: CDS
<222> LOCATION: (1)..(1146)
<220> FEATURE:
<221> NAME/KEY: mutation
<222> LOCATION: (640)..(640)

<400> SEQUENCE: 8 gag gac tgt gtc tgg gac aat gat gta gac tat cct gag tat cct cct      48
Glu Asp Cys Val Trp Asp Asn Asp Val Asp Tyr Pro Glu Tyr Pro Pro
1               5                  10                  15 ctg atc ctg gat tca tcc ttt cag ctg gtt ctg cca gtg ttg gaa gga      96
Leu Ile Leu Asp Ser Ser Phe Gln Leu Val Leu Pro Val Leu Glu Gly
            20                  25                  30 gac caa agg ata acc agt gtc caa tct ggg agt aag ctg atc ttg gct     144
Asp Gln Arg Ile Thr Ser Val Gln Ser Gly Ser Lys Leu Ile Leu Ala
        35                  40                  45 tgt cct ggg agg gga att tca gcc ctg ggg tca gag gat gca caa gcc     192
Cys Pro Gly Arg Gly Ile Ser Ala Leu Gly Ser Glu Asp Ala Gln Ala
    50                  55                  60 act tgt ctt ggt ggc aag ctc gtc gaa gtc gat ggc aaa gaa tgg aat     240
Thr Cys Leu Gly Gly Lys Leu Val Glu Val Asp Gly Lys Glu Trp Asn
65                  70                  75                  80 ata gtc gaa ctc ggc tgc aca aaa atg gca tct gaa acc atc cat aga     288
Ile Val Glu Leu Gly Cys Thr Lys Met Ala Ser Glu Thr Ile His Arg
                85                  90                  95 aac ctt gga caa tgt ggt gat caa gac ctg gga att tac gaa gtc att     336
Asn Leu Gly Gln Cys Gly Asp Gln Asp Leu Gly Ile Tyr Glu Val Ile
            100                 105                 110 ggt ttc gac ctt cca aca acg gga cac ttc tat gaa ttg ata cga gtt     384
Gly Phe Asp Leu Pro Thr Thr Gly His Phe Tyr Glu Leu Ile Arg Val
        115                 120                 125 tgc ttt gac ccg gca aat gag acc act att ttt tcc gag aac atc gtt     432
Cys Phe Asp Pro Ala Asn Glu Thr Thr Ile Phe Ser Glu Asn Ile Val
    130                 135                 140 cac gga gcc agc atc gcc gcc aaa gac att gac ccg ggt cgt cca tct     480
His Gly Ala Ser Ile Ala Ala Lys Asp Ile Asp Pro Gly Arg Pro Ser
145                 150                 155                 160 ttc aaa aca tcc act ggg ttc ttc agt gta tcg atg ata tct gtc tat     528
Phe Lys Thr Ser Thr Gly Phe Phe Ser Val Ser Met Ile Ser Val Tyr
                165                 170                 175 tcg caa aga agt cag ctg gag ctc atg aag aac ctc tta gga gat gat     576
Ser Gln Arg Ser Gln Leu Glu Leu Met Lys Asn Leu Leu Gly Asp Asp
            180                 185                 190 gaa tta gct gcg aca atc atc gat cct tca gag cag ttc tac ttt gct     624
Glu Leu Ala Ala Thr Ile Ile Asp Pro Ser Glu Gln Phe Tyr Phe Ala
        195                 200                 205 aaa gga cat atg gct gct gac gcg gac ttt gtg aca gta gtt gag cag     672
Lys Gly His Met Ala Ala Asp Ala Asp Phe Val Thr Val Val Glu Gln
    210                 215                 220 gac gca aca tac tat tac atc aac gcg ttg cct caa tgg cag gcc ttt     720
Asp Ala Thr Tyr Tyr Tyr Ile Asn Ala Leu Pro Gln Trp Gln Ala Phe
225                 230                 235                 240 aac aat gga aac tgg aag tac ttg gaa tac gac acc cgt gac ctg gct     768
Asn Asn Gly Asn Trp Lys Tyr Leu Glu Tyr Asp Thr Arg Asp Leu Ala
                245                 250                 255 gaa aaa cat ggc act gac ctg acc gtc tac agt ggt ggc tgg ggg gtt     816
Glu Lys His Gly Thr Asp Leu Thr Val Tyr Ser Gly Gly Trp Gly Val
            260                 265                 270 cta gag ctt gaa gac atc aac gga aac ccc gtt gaa atc tat ctt ggc     864
Leu Glu Leu Glu Asp Ile Asn Gly Asn Pro Val Glu Ile Tyr Leu Gly
```

-continued

```
                    275                 280                 285
ctc gcc cag gac aaa aaa gtt gtc cct gct cct gca tta aca tgg aag        912
Leu Ala Gln Asp Lys Lys Val Val Pro Ala Pro Ala Leu Thr Trp Lys
    290                 295                 300 gtg atc tat gag aag gac act aac cga gct gct gct att gtt gga ata        960
Val Ile Tyr Glu Lys Asp Thr Asn Arg Ala Ala Ala Ile Val Gly Ile
305                 310                 315                 320 aac aac ccc cac atc acc acg gca cca gaa cct ctt tgt acc gac atc       1008
Asn Asn Pro His Ile Thr Thr Ala Pro Glu Pro Leu Cys Thr Asp Ile
                325                 330                 335 tgc tcc agc ctc aca tgg ctg gac ttt gat ttt ggg gac ctt gtc cat       1056
Cys Ser Ser Leu Thr Trp Leu Asp Phe Asp Phe Gly Asp Leu Val His
            340                 345                 350 ggc tac acc tac tgc tgc tct gta gct gat ctc agg gca gcc att ccc       1104
Gly Tyr Thr Tyr Cys Cys Ser Val Ala Asp Leu Arg Ala Ala Ile Pro
        355                 360                 365 aat gtt cca gat tta gga gac gtt gat atc tta gac gaa taa               1146
Asn Val Pro Asp Leu Gly Asp Val Asp Ile Leu Asp Glu
    370                 375                 380

<210> SEQ ID NO 9
<211> LENGTH: 23
<212> TYPE: PRT
<213> ORGANISM: Pandalus borealis
<220> FEATURE:
<221> NAME/KEY: SIGNAL
<222> LOCATION: (1)..(23)

<400> SEQUENCE: 9

Met Ile Gly Arg Thr Thr Phe Ile Ala Leu Phe Val Lys Val Leu Thr
1               5                   10                  15

Ile Trp Ser Phe Thr Lys Gly
            20

<210> SEQ ID NO 10
<211> LENGTH: 15
<212> TYPE: DNA
<213> ORGANISM: Artificial
<220> FEATURE:
<223> OTHER INFORMATION: 5' FAM and 3' TAMRA labelled oligonucleotide
      probe for measuring DNase activity

<400> SEQUENCE: 10
cgccatcgga ggttc                                                        15

<210> SEQ ID NO 11
<211> LENGTH: 15
<212> TYPE: DNA
<213> ORGANISM: Artificial
<220> FEATURE:
<223> OTHER INFORMATION: complementary sequence of SEQ ID No. 10

<400> SEQUENCE: 11
gaacctccga tggcg                                                        15

<210> SEQ ID NO 12
<211> LENGTH: 18
<212> TYPE: DNA
<213> ORGANISM: Artificial
<220> FEATURE:
<223> OTHER INFORMATION: Forward primer for amplifying a section of the
      E. coli 23SrRNA gene

<400> SEQUENCE: 12
gaaaggcgcg cgatacag                                                     18
```

```
<210> SEQ ID NO 13
<211> LENGTH: 19
<212> TYPE: DNA
<213> ORGANISM: Artificial
<220> FEATURE:
<223> OTHER INFORMATION: Reverse primer for amplifying a section of the
      E. coli 23SrRNA

<400> SEQUENCE: 13
gtcccgccct actcatcga                                                     19

<210> SEQ ID NO 14
<211> LENGTH: 26
<212> TYPE: DNA
<213> ORGANISM: Artificial
<220> FEATURE:
<223> OTHER INFORMATION: 5' FAM and 3' BHQ labelled oligonucleotide
      probe complementary to a section of the E. coli 23SrRNA gene
      between the regions complementary to SEQ ID No. 13 and SEQ ID No.
      14

<400> SEQUENCE: 14
ccccgtacac aaaaatgcac atgctg                                             26

<210> SEQ ID NO 15
<211> LENGTH: 381
<212> TYPE: PRT
<213> ORGANISM: Paralithodes camtschatica

<400> SEQUENCE: 15
```

| Gln | Asp | Cys | Val | Trp | Asp | Lys | Asp | Thr | Asp | Phe | Pro | Glu | Asp | Pro | Pro |
|---|---|---|---|---|---|---|---|---|---|---|---|---|---|---|---|
| 1 | | | | 5 | | | | | 10 | | | | | 15 | |

| Leu | Ile | Phe | Asp | Ser | Asn | Leu | Glu | Leu | Ile | Arg | Pro | Val | Leu | Glu | Asn |
|---|---|---|---|---|---|---|---|---|---|---|---|---|---|---|---|
| | | | 20 | | | | | 25 | | | | | 30 | | |

| Gly | Lys | Arg | Ile | Val | Ser | Val | Pro | Ser | Gly | Ser | Ser | Leu | Thr | Leu | Ala |
|---|---|---|---|---|---|---|---|---|---|---|---|---|---|---|---|
| | | 35 | | | | | 40 | | | | | 45 | | | |

| Cys | Ser | Gly | Ser | Glu | Leu | Ile | Asn | Leu | Gly | Met | Glu | Ala | Val | Glu | Ala |
|---|---|---|---|---|---|---|---|---|---|---|---|---|---|---|---|
| | 50 | | | | | 55 | | | | | 60 | | | | |

| Lys | Cys | Ala | Gly | Gly | Val | Met | Leu | Ala | Ile | Glu | Gly | Thr | Glu | Trp | Glu |
|---|---|---|---|---|---|---|---|---|---|---|---|---|---|---|---|
| 65 | | | | | 70 | | | | | 75 | | | | | 80 |

| Ile | Trp | Ser | Leu | Gly | Cys | Ser | Asn | His | Val | Lys | Glu | Thr | Ile | Arg | Arg |
|---|---|---|---|---|---|---|---|---|---|---|---|---|---|---|---|
| | | | | 85 | | | | | 90 | | | | | 95 | |

| Asn | Leu | Gly | Thr | Cys | Gly | Glu | Ala | Asp | Gln | Gly | Asp | Arg | His | Ser | Ile |
|---|---|---|---|---|---|---|---|---|---|---|---|---|---|---|---|
| | | | 100 | | | | | 105 | | | | | 110 | | |

| Gly | Phe | Glu | Tyr | Tyr | Gly | Gly | Ser | Ile | Tyr | Tyr | Glu | Leu | Ile | Ser | Val |
|---|---|---|---|---|---|---|---|---|---|---|---|---|---|---|---|
| | | 115 | | | | | 120 | | | | | 125 | | | |

| Cys | Phe | Gly | Pro | Val | Ser | Glu | Thr | Thr | Leu | Arg | Thr | Glu | His | Val | Leu |
|---|---|---|---|---|---|---|---|---|---|---|---|---|---|---|---|
| | 130 | | | | | 135 | | | | | 140 | | | | |

| His | Gly | Ala | Asn | Ile | Ala | Ala | Lys | Asp | Ile | Glu | Thr | Ser | Arg | Pro | Ser |
|---|---|---|---|---|---|---|---|---|---|---|---|---|---|---|---|
| 145 | | | | | 150 | | | | | 155 | | | | | 160 |

| Phe | Lys | Thr | Ser | Thr | Gly | Phe | Phe | Ser | Val | Ser | Met | Ser | Thr | Val | Tyr |
|---|---|---|---|---|---|---|---|---|---|---|---|---|---|---|---|
| | | | | 165 | | | | | 170 | | | | | 175 | |

| Ser | Gln | Ala | Ser | Gln | Leu | Gln | Leu | Met | Thr | Asp | Ile | Leu | Gly | Asp | Ser |
|---|---|---|---|---|---|---|---|---|---|---|---|---|---|---|---|
| | | | 180 | | | | | 185 | | | | | 190 | | |

| Asp | Leu | Ala | Asn | Asn | Ile | Ile | Asp | Pro | Ser | Gln | Gln | Leu | Tyr | Phe | Ala |
|---|---|---|---|---|---|---|---|---|---|---|---|---|---|---|---|
| | | 195 | | | | | 200 | | | | | 205 | | | |

| Lys | Gly | His | Met | Ser | Pro | Asp | Ala | Asp | Phe | Val | Thr | Val | Ala | Glu | Gln |
|---|---|---|---|---|---|---|---|---|---|---|---|---|---|---|---|
| | 210 | | | | | 215 | | | | | 220 | | | | |

| Asp | Ala | Thr | Tyr | Tyr | Phe | Ile | Asn | Ala | Leu | Pro | Gln | Trp | Gln | Ala | Phe |
|---|---|---|---|---|---|---|---|---|---|---|---|---|---|---|---|

-continued

```
            225                 230                 235                 240
Asn Asn Gly Asn Trp Lys Tyr Leu Glu Tyr Ala Thr Arg Asp Leu Ala
                245                 250                 255
Glu Ser His Gly Ser Asp Leu Arg Val Tyr Ser Gly Gly Trp Ser Leu
                260                 265                 270
Leu Gln Leu Asp Asp Ile Asn Gly Asn Pro Val Asp Ile Leu Leu Gly
            275                 280                 285
Leu Ser Glu Gly Lys Glu Val Val Pro Val Pro Ser Leu Thr Trp Lys
        290                 295                 300
Val Val Tyr Glu Glu Ser Ser Ser Lys Ala Ala Ala Ile Val Gly Ile
305                 310                 315                 320
Asn Asn Pro His Ile Thr Thr Ala Pro Ser Pro Leu Cys Ser Asp Leu
                325                 330                 335
Cys Ser Ser Leu Thr Trp Ile Asp Phe Asn Leu Asp Asp Leu Ala His
                340                 345                 350
Gly Tyr Thr Tyr Cys Cys Ala Val Asp Asp Leu Arg Gln Ala Ile Pro
            355                 360                 365
Tyr Ile Pro Asp Leu Gly Asn Val Gly Leu Leu Thr Asn
    370                 375                 380
```